US012138393B2

(12) United States Patent
McCormick et al.

(10) Patent No.: US 12,138,393 B2
(45) Date of Patent: Nov. 12, 2024

(54) VENTILATOR SYSTEMS AND METHODS

(71) Applicant: GE Precision Healthcare LLC, Wauwatosa, WI (US)

(72) Inventors: Timothy P. McCormick, Madison, WI (US); Erkki Paavo Olavi Heinonen, Helsinki (FI); Kimberly Brauer, Madison, WI (US); Tom J. Haggblom, Helsinki (FI)

(73) Assignee: GE Precision Healthcare LLC, Wauwatosa, WI (US)

( * ) Notice: Subject to any disclaimer, the term of this patent is extended or adjusted under 35 U.S.C. 154(b) by 954 days.

(21) Appl. No.: 17/168,032

(22) Filed: Feb. 4, 2021

(65) Prior Publication Data

US 2022/0241539 A1  Aug. 4, 2022

(51) Int. Cl.
*A61M 16/08* (2006.01)
*A61M 16/00* (2006.01)
(Continued)

(52) U.S. Cl.
CPC .... *A61M 16/0816* (2013.01); *A61M 16/0057* (2013.01); *A61M 16/01* (2013.01);
(Continued)

(58) Field of Classification Search
CPC .............. A61M 16/00; A61M 16/0051; A61M 16/0057; A61M 16/0063; A61M 16/0066; A61M 16/0075; A61M 16/0078; A61M 16/0081; A61M 16/0084; A61M 16/009; A61M 16/0096; A61M 16/01; A61M 16/024; A61M 16/04; A61M 16/06; A61M 16/0672; A61M 16/08; A61M 16/0816; A61M 16/0833; A61M 16/0841; A61M 16/085; A61M 16/0858; A61M 16/10; A61M 16/1005; A61M 16/1015; A61M 16/104; A61M 16/12; A61M 16/125; A61M 16/14; A61M 16/16; A61M 16/20;
(Continued)

(56) References Cited

U.S. PATENT DOCUMENTS 1,005,816 A    10/1911  Drager
4,883,051 A *  11/1989  Westenskow ..... A61M 16/0858
                                          128/205.15
(Continued)

OTHER PUBLICATIONS

EP patent application 22153128.8 filed Jan. 25, 2022—extended Search Report issued Jul. 6, 2022; 10 pages.

*Primary Examiner* — Annette Dixon
(74) *Attorney, Agent, or Firm* — Andrus Intellectual Property Law, LLP

(57) ABSTRACT

A ventilator system includes a ventilator and a host. The ventilator comprises a ventilation drive configured to drive ventilation gas from a gas source to a patient and a patient interface section configured to guide inspiratory gas along an inspiratory path from the ventilation drive to a patient connection, and guide expiratory gas along an expiratory path from the patient connection out of the ventilator. The patient interface section is configured to releasably connect to the ventilation drive. The ventilator is configured to removably connect to the host such that at least one of the inspiratory path and the expiratory path are diverted through the host when the ventilator is removably connected to the host.

21 Claims, 12 Drawing Sheets

(51) Int. Cl.
*A61M 16/01* (2006.01)
*A61M 16/04* (2006.01)
*A61M 16/06* (2006.01)

(52) U.S. Cl.
CPC ............ *A61M 16/04* (2013.01); *A61M 16/06* (2013.01); *A61M 16/0666* (2013.01); *A61M 2205/3584* (2013.01); *A61M 2205/3592* (2013.01); *A61M 2205/502* (2013.01); *A61M 2205/8206* (2013.01); *A61M 2209/10* (2013.01)

(58) Field of Classification Search
CPC .............. A61M 16/204; A61M 16/205; A61M 16/208; A61M 16/209; A61M 16/22; A61M 2016/0018; A61M 2016/0027; A61M 2016/0039; A61M 2016/0042; A61M 2016/102; A61M 2016/1025; A61M 2016/1035; A61M 2202/0208; A61M 2202/0225; A61M 2202/0241; A61M 2202/0275; A61M 2202/0283; A61M 2205/07; A61M 2205/18; A61M 2205/3382; A61M 2205/50; A61M 2205/8206; A61M 2209/084; A61M 2209/10; A61M 2230/432
See application file for complete search history.

(56) References Cited

U.S. PATENT DOCUMENTS

| | | | | |
|---|---|---|---|---|
| 5,673,688 | A * | 10/1997 | Tham | A61M 16/104 128/204.22 |
| 6,095,138 | A * | 8/2000 | Hognelid | A61M 16/0063 128/204.21 |
| 6,158,430 | A | 12/2000 | Pfeiffer et al. | |
| 6,213,120 | B1 * | 4/2001 | Block | A61M 16/0075 128/204.23 |
| 6,227,196 | B1 * | 5/2001 | Jaffe | A61B 5/029 600/587 |
| 6,474,333 | B1 * | 11/2002 | Heinonen | A61M 16/10 128/204.26 |
| 8,800,557 | B2 * | 8/2014 | Andreiux | A61M 16/208 128/204.23 |
| 10,471,229 | B2 | 11/2019 | McCormick | |
| 2008/0264417 | A1 * | 10/2008 | Manigel | A61M 16/0063 128/205.12 |
| 2016/0058967 | A1 | 3/2016 | McCormick et al. | |
| 2020/0129721 | A1 | 4/2020 | Tappehorn et al. | |
| 2020/0353200 | A1 * | 11/2020 | McCormick | A61M 16/22 |
| 2022/0241527 | A1 * | 8/2022 | McCormick | A61M 16/024 |

* cited by examiner

VENTILATOR SYSTEMS AND METHODS

BACKGROUND

The present disclosure is related to the field of patient ventilation, including mechanical ventilation, and more particularly to a portable ventilation drive and adaptable ventilation system to facilitate ventilation of a patient in multiple different settings where mechanical ventilation or other respiratory support is required.

Over the course of a medical treatment, a patient may require some form of respiratory support provided by a ventilator or may require multiple different types of respiratory support which is generally provided by different types of ventilation devices in different settings. Respiratory support may include assisted breathing, wherein the ventilator detects breath attempts and provides supplemental pressure and gas flow for the patient to complete and effective respiratory cycle. Other forms of respiratory support include mechanical ventilation, whereby the ventilator also initiates the respiratory phase of each respiratory cycle.

Different types of mechanical ventilators are available that each provide mechanical ventilation for a particular setting, such as an intensive care ventilator configured to provide mechanical ventilation support for an extended duration of time and an operating room ventilator configured to provide anesthetic gas to the patient and to provide respiratory support to the patient while they are under general anesthesia. During treatment, the patient receiving respiratory support may need to be transferred between ventilator systems. One example of this transfer may occur when a patient is switched between receiving respiratory support from an anesthesia ventilator used during surgery to an intensive care unit (ICU) ventilator to which the patient may be connected before and/or after the surgical procedure. This transfer necessarily requires disconnection of the patient from one ventilator before connection to another, leaving a period when the patient is disconnected from receiving respiratory support from either ventilator. This connection and disconnection of the patient also exposes the patient's airway to pathogens and can lead to acquisition of a nosocomial infection.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a portable ventilator includes a ventilation drive configured to drive ventilation gas from a gas source to a patient, wherein the portable ventilator is configured to removably connect to a host such that when the portable ventilator is connected to the host the ventilation drive drives ventilation gas from a host gas source to the patient and when the portable ventilator is not connected to the host the ventilation drive drives ventilation gas from a portable gas source to the patient.

One embodiment of a patient ventilation system includes a first host connected to a first host gas source, a portable ventilator configured to removably connect to the first host, and a portable gas source connected to the portable ventilator. The portable ventilator includes a ventilation drive configured to drive ventilation gas from the first host gas source to a patient when the portable ventilator is connected to the first host and to drive ventilation gas from the portable gas source to the patient when the portable ventilator is not connected to the first host.

In certain examples, the inspiratory gas from the portable gas source is at a first pressure and the inspiratory gas from the anesthesia gas source is at a second pressure, wherein the second pressure is greater than the first pressure. In certain embodiments, the portable ventilator may further comprise a portable gas source input valve configured to automatically open to allow the ventilation gas to flow from the portable gas source when the portable ventilator is not connected to the host gas source. For example, the portable gas source input valve may be configured to open when a delivery pressure of ventilation gas from the host gas source is lower than a delivery pressure of ventilation gas from the portable gas source.

In certain embodiments, the portable ventilator may include a ventilation drive section and a patient interface section. In certain examples, the ventilation drive section and a patient interface section may be configured to removably connect together and may be separable for cleaning and/or maintenance.

One embodiment of a method of ventilator operation includes operating a ventilation drive of a portable ventilator to drive ventilation gas from a portable gas source through a patent interface to a patient, wherein the ventilation gas from the portable gas source is at a first pressure. Upon connection of the portable ventilator to a host, the ventilation drive is operated to drive ventilation gas from a host gas source through the patent interface to the patient, wherein the ventilation gas from the host gas source is at a second pressure, wherein the second pressure is greater than the first pressure. In certain examples, the ventilation drive may automatically revert back to driving ventilation gas from the portable gas source through the patent interface to the patient upon the second pressure of the host gas source becoming less than the first pressure of the host gas source.

One embodiment of a ventilator includes a ventilation drive configured to drive ventilation gas from a gas source to a patient and a patient interface section configured to guide inspiratory gas from the ventilation drive to a patient connection, receive expiratory gas from the patient connection, and expel the expiratory gas out of the ventilator. The ventilation drive and patient interface section are configured to removably connect to at least one host comprising a ventilation path portion so as to divert the inspiratory gas through the ventilation path portion of the host when connected thereto.

In one embodiment, the host may be an anesthesia host comprising a circle breathing system and the ventilation drive is configured to removably connect to the anesthesia host and the circle breathing system. In certain examples, the ventilation drive may be configured to drive inspiratory gas from a host gas source, such as an anesthesia gas source, through the patient interface section to the patient when connected to the host, and to drive inspiratory gas from a portable gas source through the patent interface section to the patient when the ventilator is not connected to the host.

One embodiment of an anesthesia ventilator system includes a portable ventilator comprising a ventilation drive configured to drive inspiratory gas from a gas source to a patient and a patient interface section configured to guide inspiratory gas from the ventilation drive to a patient connection, receive expiratory gas from the patient connection, and expel the expiratory gas out of the portable ventilator. The anesthesia ventilator system further includes a circle breathing system, a scavenging system, and a host gas source. The portable ventilator is configured to removably connect to the circle breathing system, the scavenging system, and the host gas source, wherein the ventilation drive is configured to drive inspiratory gas from the host gas source to the patient through the patient interface section when connected, and to drive inspiratory gas from a portable gas source to the patient through the patent interface section when disconnected.

One embodiment of a method of ventilator operation includes operating a ventilation drive to drive inspiratory gas through a patent interface section to a patient. Upon connection of the ventilation drive and the patient interface section to an a host comprising a ventilation path portion, operating the ventilation drive to drive inspiratory gas from an anesthesia gas source through the ventilation path portion and the patent interface section to the patient.

In certain embodiments, upon connection of the ventilation drive and/or the patient interface section to the host, a host source connection valve is opened to facilitate flow of inspiratory gas from a host gas source to the ventilation drive and closing a portable gas source input valve to stop flow of inspiratory gas from the portable gas source to the ventilation drive. In further embodiments, upon connection of the ventilation drive and/or the patient interface section to the host, at least one inspiratory diverter valve in the patient interface section is opened, wherein the inspiratory diverter valve is configured to divert the inspiratory gas from the patient interface section through the circle breathing system.

In one embodiment, a ventilator system includes a ventilator and a host. The ventilator comprises a ventilation drive configured to drive ventilation gas from a gas source to a patient and a patient interface section configured to guide inspiratory gas along an inspiratory path from the ventilation drive to a patient connection, and guide expiratory gas along an expiratory path from the patient connection out of the ventilator. The patient interface section is configured to releasably connect to the ventilation drive. The ventilator is configured to removably connect to the host such that at least one of the inspiratory path and the expiratory path are diverted through the host when the ventilator is removably connected to the host. In certain embodiments, the expiratory path does not enter the ventilation drive such that the ventilation drive does not receive any patient expiratory gas and, in further embodiments, the patient interface section is separately removable from the ventilator system while the ventilation drive is connected to the host and is a cleanable and sterilizable unit.

One embodiment of a ventilator includes a ventilation drive configured to drive ventilation gas from a gas source to a patient and a patient interface section configured to guide inspiratory gas along an inspiratory path from the ventilation drive to a patient connection, and guide expiratory gas along an expiratory path from the patient connection out of the ventilator. The patient interface section is configured to releasably connect to the ventilation drive. The ventilation drive is configured to removably connect to a host such that when the ventilation drive is connected to the host the ventilation drive is configured to drive inspiratory gas from a host gas source through the patient interface section to the patient, and when the ventilation drive is not connected to the host the ventilation drive is configured to drive inspiratory gas from a portable gas source through the patient interface section to the patient.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1:
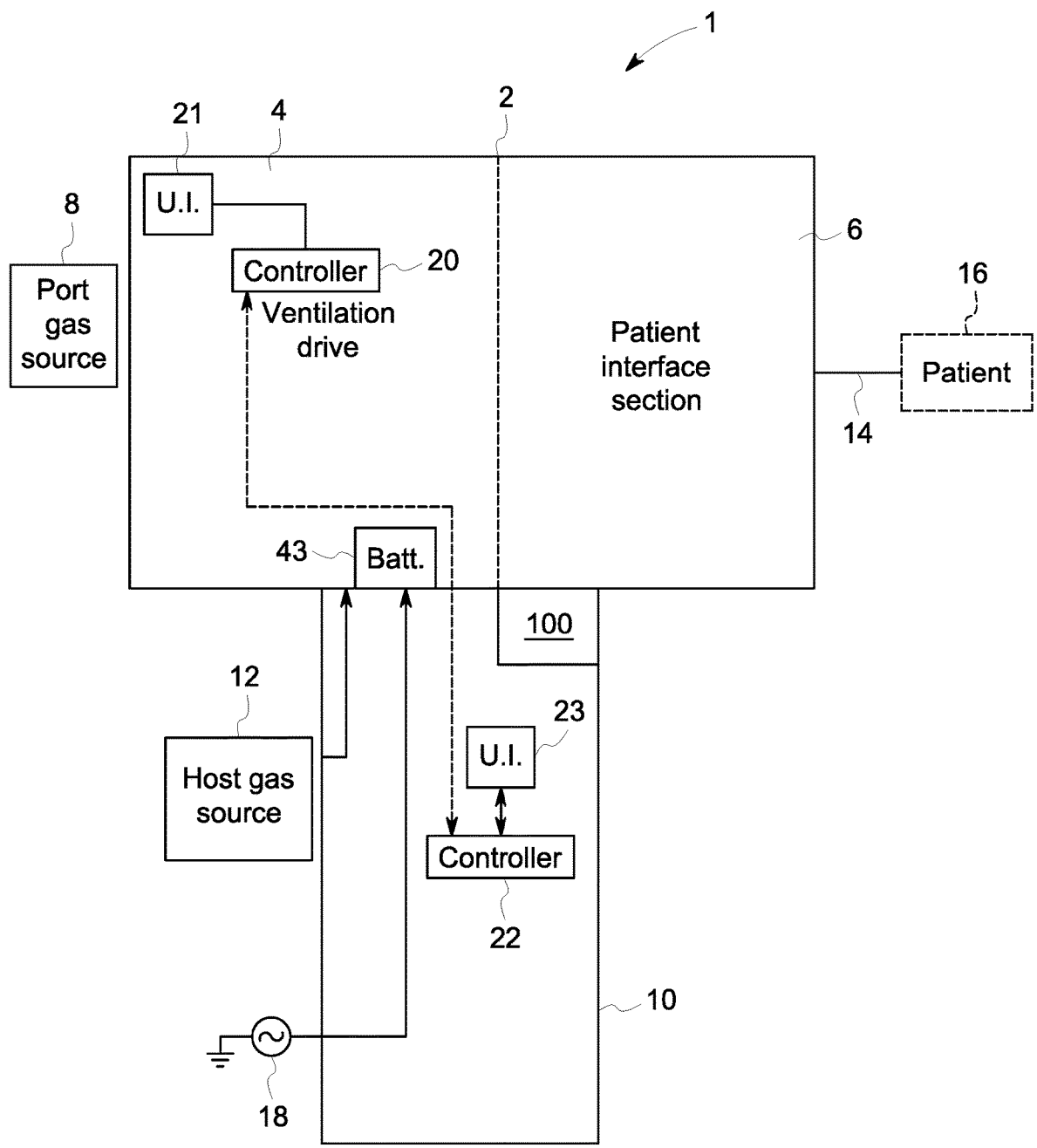
FIG. 1 is a system diagram of an exemplary embodiment of a ventilator system according to the present disclosure.

The inventors have identified that several challenges exist for providing continuous respiratory support to a patient, particularly when an intubated patient must be transferred between ventilators. One major issue is continuous maintenance of positive end expiratory pressure (PEEP), another is infection avoidance as described above. Further, the inventors have recognized that the best patient care can be provided when a consistent and continuous ventilation connection is maintained, including constant connection to the ventilator via the patient connection device(s) and utilizing consistent ventilation parameters with no break in continuity.

Maintenance of PEEP is an important aspect of continuous mechanical ventilation, especially when the patient is receiving lung volume recruitment therapy. Certain medical conditions, including but not limited to atelectasis, result in collapsed alveoli. Collapsed alveoli can create a significant loss of lung volume and impair the efficiency of gas exchange. Typically, the gas exchange removes carbon dioxide from the patient's blood while introducing oxygen to the patient's blood. Specialized forms of respiratory support known as recruitment procedures have been developed to progressively open or "recruit" collapsed alveoli. Recruitment procedures may use specialized medical gases such as helium in addition to other medical gases of oxygen, nitrogen and air or other additives such as surfactant to reduce airway resistance. Still, recruitment procedures typically involve a series of prescribed ventilation pressure, including, but not limited to inspiratory pressure and expiratory pressure. PEEP is a common component of a prescribed recruitment procedure. PEEP puts a positive pressure on the patient's airway at the end of an expiratory phase of a breathing cycle to "hold open" open alveoli which would normally collapse under ambient pressure. Thus, the PEEP therapy preserves recruited lung volume, maintaining the lung volume gains achieved through the recruitment procedure.

Recruitment procedures typically occur over a prescribed period of time which may be hours or days. The recruitment procedure must take place over a time period as patients in need of lung recruitment typically also have low lung compliance and the recruited volume is desired to be gained from opening of alveoli rather than lung distension. Therefore, the recruitment procedure slowly increases the pressure applied to the lung over time as more alveoli are recruited and lung volume is gained.

However, as noted above, typically when a patient is transferred between ventilators at some point in the transition the patient must be disconnected from one ventilator and reconnected to the other ventilator. Even if this transition period is a short period of time (e.g., within seconds) the loss of the PEEP maintained in the system can cause the recruited alveoli to collapse, giving up any physiological gains that have been made through the previous recruitment procedure and other respiratory support. A new recruitment procedure or procedures must be performed over the aforementioned hours or days in order to re-recruit the lost lung volume. Therefore, embodiments of the portable ventilator 2 disclosed herein preserves the numeric conditions of the patient such that recruited lung volume is maintained and constant ventilation is performed.

The inventors have recognized that it is beneficial to the patient to maintain full ventilation functionality at all times, including oxygen supply and continuous and consistent ventilation pressure and ventilation parameters. The inventors developed the disclosed solution based on the above described problems and challenges in the relevant art of patient ventilation. In the disclosed system and method, one ventilation drive and patient connection thereto is continuously maintained such that the patient is continuously ventilated and no disconnection of the patient is ever necessary. The portable ventilator 2 and ventilation system 1 described herein allows continuous use of the same ventilation drive 4 and patient interface section 6, which connect and disconnect from various hosts.

The portable ventilator 2 also operates on its own to provide full ventilation support to the patient, including full mechanical ventilation, assisted ventilation support, peep, etc. The portable ventilator 2 can attach to any of the various portable ventilation gas sources, such as oxygen tanks or wall gas, and can travel with the patient, such as when being transported between the surgical ward and the ICU, etc. The portable ventilator 2 can also connect to a host providing a high pressure gas source, such as a large oxygen cylinder or wall gas, to provide extended duration ventilation. The portable ventilator 2 may be configured to automatically utilize a host gas source 12 when connected thereto when the host 10, provided that the host gas source 12 is available and functioning. The portable ventilator 2 may be configured to automatically revert to independent function and/or maintenance of ventilation from a portable gas source 8 whenever the portable ventilator 2 is disconnected from a host and/or the host gas source 12 is unavailable (e.g. is empty or has malfunctioned).

The portable ventilator 2 connects to any one of a plurality of hosts, alternately one at a time, in order to provide additional ventilation functions for particular situations, such as extended ICU ventilation, specialized ventilation maneuvers or tests, or anesthesia-related ventilation during surgical or other procedure. Thus, the portable ventilator is configured to connect to a plurality of different host types with differing ventilation functionalities depending on the patient care needs. The portable ventilator may be correspondingly designed with the various host types to enable connection and disconnection of the portable ventilator from each of the various hosts, one at a time.

In the embodiment at FIG. 1, the ventilation system 1 includes a portable ventilator 2 removably connectable to one or more hosts, alternately one at a time. A portable gas source 8 is connected to the portable ventilator 2 and a host gas source 12 is connected to the host 10. The portable ventilator 2 is configured to deliver ventilation gas to the patient 16 from either one of at least one portable gas source 8 and a host gas source 12. For example, the portable ventilator 2 may be configured to deliver ventilation gas from the host gas source 12 whenever the portable ventilator 2 is connected to the host 10 and to deliver ventilation gas from the portable gas source 8 to the patient 16 whenever the portable ventilator 2 is not connected to any host. In certain embodiments, the host gas source 12 may be regulated at a higher delivery pressure of ventilation gas compared to the portable gas source 8 and the portable ventilator 2 may be configured to drive ventilation gas to the patient from whichever gas source is available and has the highest delivery pressure.

The portable ventilator 2 may include a ventilation drive 4 and a patient interface section 6. The ventilation drive 4 is configured to drive ventilation gas from a gas source, which may be a portable gas source 8 directly to the portable ventilator 2 or a host gas source 12 connected to a host 10 to which the portable ventilator 2 is connected. The ventilation drive 4 drives the ventilation gas through the patient interface section 6 to the patient 16. The patient interface section 6 is configured to deliver inspiratory gas from the ventilation drive 4 to the patient 16 and to receive expiratory gas exhaled by the patient 16. The patient interface section 6 is further configured to expel the expiratory gas out of the portable ventilator 2, which may be expelled to atmosphere or, in some embodiments, delivered to a scavenging system or delivered to the host 10 for further processing and/or recirculation to the patient (e.g. scavenging and/or $CO_2$ scrubbing and recirculation to the patient). The patient interface section 6 includes an inspiratory path 60 providing ventilation gas to be inhaled by the patient (inspiratory gas) from the ventilation drive 4 to the patient 16. The patient interface section 6 further includes and defines an expiratory path 70 that receives expiratory gases exhaled from the patient 16 and expels the exhalation gas out of the portable ventilator 2.

Figure 2A:
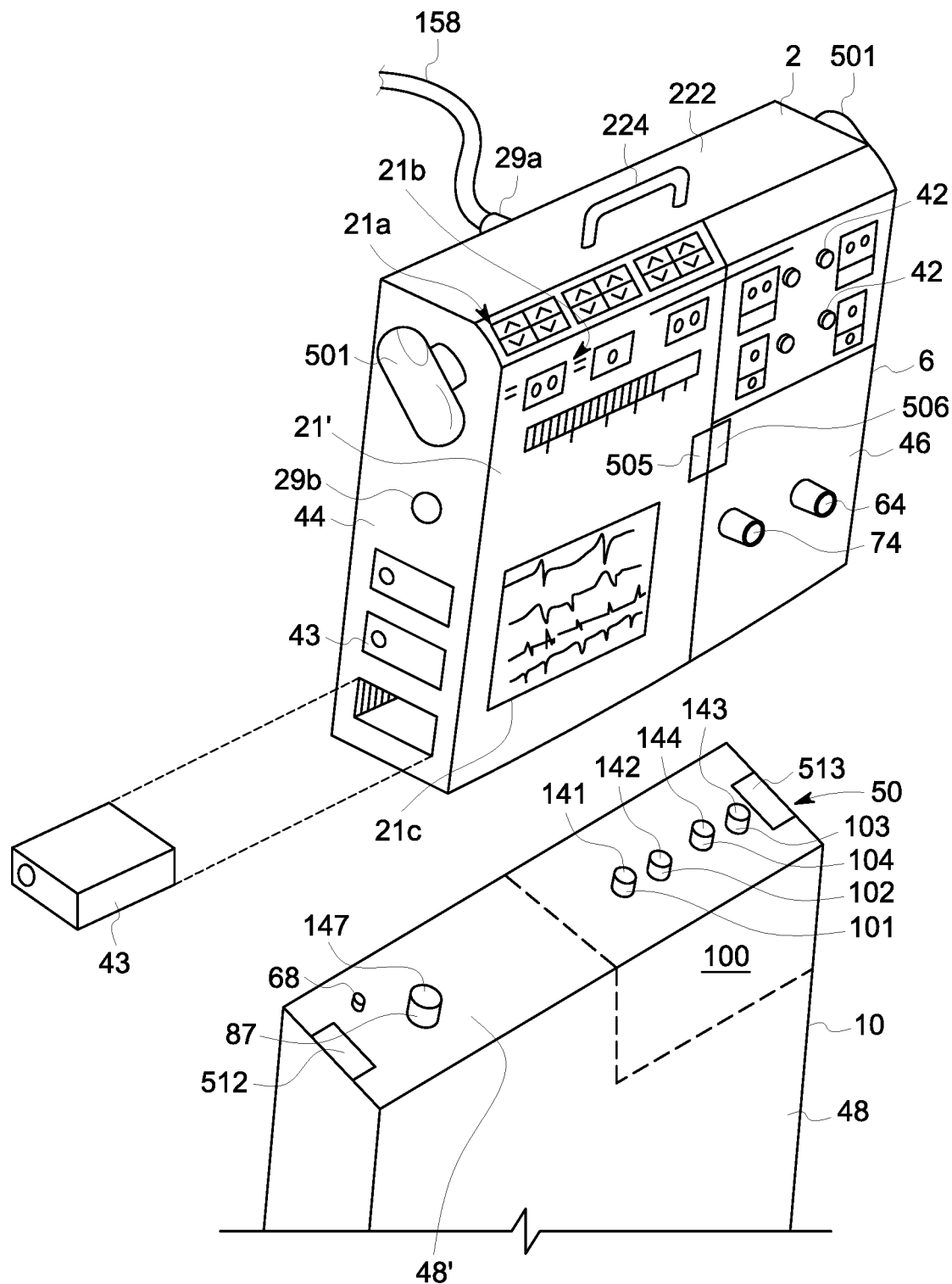
FIGS. 2A and 2B depict an exemplary embodiment of a portable ventilator that removably connects to a host according to the present disclosure.
Figure 5:
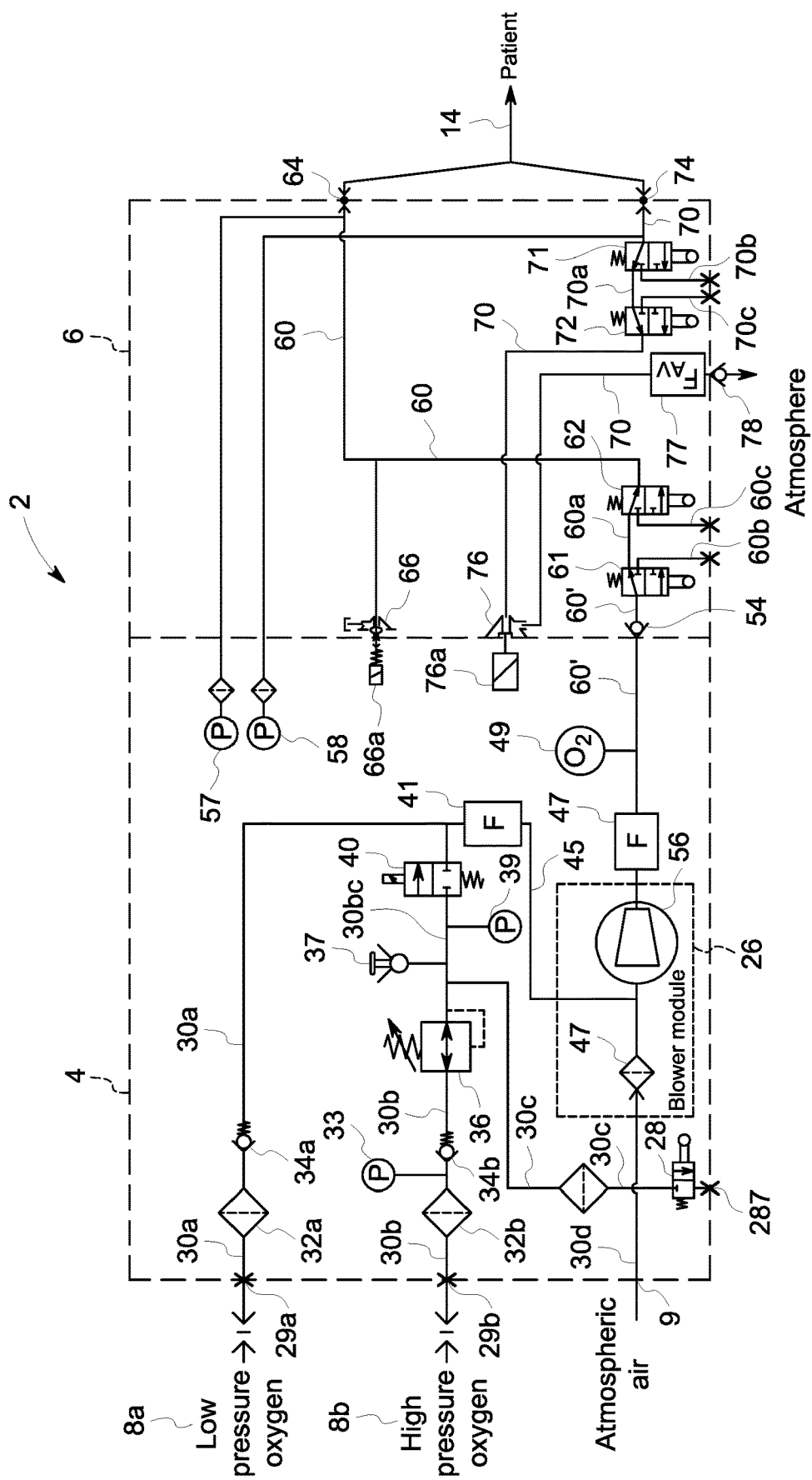
FIG. 5 is a system diagram depicting one embodiment of ventilator pneumatics according to the present disclosure.

Referring also to FIGS. 2A and 5, the patient interface section 6 has an inspiratory connection port 64 that connects to an inspiratory portion of a patient connection 14 to deliver the inspiratory gas to the patient's lungs. An expiratory connection port 74 connects between an expiratory portion of the patient 16 and the patient interface section 6 to deliver expiratory gas exhaled by the patient to the expiratory path 70. In embodiments, the patient connection 14 may include, for example, an endotracheal (ET) tube. In such embodiments, the patient connection is one that creates a pneumatic seal with the airway of the patient. Such a pneumatic seal enables the control and delivery of flows of medical gas and prescribed pressures into the respiratory system of the patient. In other embodiments, the patient connection 14 may include any patient end connector configured to deliver appropriate ventilation or respiratory support to a patient, such as a mask, nasal cannula, etc.

As will be described in further detail herein, various pressures within the patient's airway, including but not limited to inspiratory pressure and expiratory pressure, may be controlled during ventilation. A flow of medical gas and/or other ventilation gases is provided through the inspiratory path 60 to the patient 16 through the patient connection 14 in an inspiratory phase of a ventilation cycle and expired gases are directed from the patient 16 through the patient connection 14 through the expiratory path 70 in an expiratory phase of the ventilation cycle. The ventilation drive 4 may include a ventilation drive means, such as a blower 56 configured to drive inspiratory gas to the patient 16. The blower 56, or other drive means, may be controlled based on measured pressures and/or flow rates within the portable ventilator 2.

In one embodiment, the patient interface section 6 is the only portion of the portable ventilator 2 that interfaces with the patient exhalation gas. Namely, in some embodiments the expiratory path 70 does not enter the ventilation drive 4 and thus contaminants from the expiratory path 70 do not enter or otherwise reach the drive 4. However, in certain embodiments sensors, actuators, and/or other electronic devices that may sense or flow within the expiratory path may be located within the ventilation drive 4 section of the portable ventilator 2. For instance, one or more pressure sensors 57, 58 configured to sense pressure within the inspiratory path 60 or expiratory path 70 (referred to together as paths 60 and 70) may be located in the ventilation drive 4 section. For instance, inspiratory pressure sensor 57 may be situated within the ventilation drive 4 and configured to sense a pressure within the expiratory path 70 in the patient interface section 6, such as near the port 64 connecting to the patient connection 14. Similarly, an expiratory pressure sensor 58 may be situated within the ventilation drive 4 and configured to sense a pressure within the expiratory path 70, such as near port 74.

One or more valve actuators that actuate valves in paths 60 and 70 may also be located in the drive portion. In certain embodiments, the patient interface section 6 may be removable from the drive section and may be a cleanable and sterilizable module since it interfaces with the patient exhalation gases. The ventilation drive 4 may be cleanable in that the housing and connection points or interfaces that connect with the patient interface section 6 are cleanable, and particularly that interface with the expiratory path 70 or otherwise can become contaminated by the exhalation gases. However, in certain embodiments the ventilation drive 4 is not sterilizable and/or autoclavable and thus does not include passageways that receive contaminated gas, such as exhalation gas from the patient.

Referring again to FIG. 1 and FIGS. 2-4B (and also to FIGS. 6 and 7), various hosts 10, 10a, 10b, 10c may be incorporated within the ventilation system 1. The portable ventilator 2 may be configured to connect with any various types of hosts 10, 10a, 10b, 10c providing different functions including but not limited to high volume and high pressure gas sources to sustain long-term ICU ventilation, and anesthesia delivery in mechanical ventilation for maintaining a patient under general anesthesia. The portable ventilator 2 is configured to connect to each of such multiple types of hosts 10, 10a, 10b, 10c to act as the ventilation drive for that host device to deliver ventilation gas from the host gas source 12 to the patient 16. The term "host 10" is used herein to refer generically to a host, which may in various embodiments by any of the host-types described herein, including hosts 10a, 10b, and 10c. In certain embodiments, the portable ventilator 2 is further configured to provide an inspiratory path that intersects with a ventilation path portion 100 of the host 10. Alternatively or additionally, the portable ventilator 2 may provide and connect to the host 10 such that the expiratory gases from the patient are diverted to a ventilation path portion 100 of the host 10. For example, in certain embodiments the host 10 may include a circle system for anesthesia delivery wherein the inspiratory pathways and expiratory pathways flow through the host 10 and connect to the pathways in the patient interface section 6. In another example, the ventilation path portion 100 may only connect to the inspiratory pathway and may provide on/off valves, such as P01 valves as shown and described herein.

Each of the at least one host 10 includes a ventilator connection section 50 configured to removably receive the portable ventilator 2 and to connect the ventilation drive 4 and patient interface section 6 to the ventilation path portion 100 in the host 10 such that ventilation drive 4 receives the host gas and the patient interface section 6 interfaces as necessary with the ventilation path portion of the host. Pneumatic diagrams of a portable ventilator 2 and pneumatic connections to various host embodiments are shown in FIGS. 5-8.

Additionally, the host may be configured to deliver power and/or communicate sensor and control information back and forth to and from the portable ventilator 2. For example, the portable ventilator 2 may include a ventilatory controller 20 in communication with a user interface 21 on or associated with the portable ventilator 2. For example, the user interface 21 may include devices through which a clinician can control ventilation parameters, such as pressure, breath rate, path flow rate, peak, and the like. Such input devices may include dials, buttons, or may be a touch screen configured to receive such input values from a clinician. The user interface 21 may also include a display configured to display ventilation information, including the various ventilation control settings, as well as patient information, such as certain patient monitoring information.

FIG. 2A illustrates an exemplary embodiment of a portable ventilator 2 disconnected from the host 10. The portable ventilator 2 has a ventilator housing 222 encapsulating the portable ventilator 2 and providing various connections and interfaces. The ventilator housing 222 includes a user interface section 21' providing various user interface devices and systems through which the user can interact with elements of the portable ventilator 2 and see different patient parameters. The user interface 21 includes ventilator control inputs 21a, including buttons, dials, knobs, and the like that enable manual control of the portable ventilator 2 functions by a clinician. The user interface 21 further includes a numerical display area 21b providing alphanumeric displays of values, such as ventilator control values and parameters. The numerical display area 21b may include, for example, numeric LED displays. Alternatively or additionally, the user interface 21 on the portable ventilator 2 may further include a ventilator display 21c configured to display patient monitoring parameters for the patient 16, as well as ventilation parameters and any other relevant control or function information for the portable ventilator 2 and/or a connected host 10.

In certain embodiments, the ventilator controller 20 of the portable ventilator 2 may be configured to communicate with the host controller 22 of a host. The host 10 may further include a user interface 23 which may also be configured to allow a clinician to set ventilation parameters, which may include ventilation parameters that can be set at the ventilator user interface 21, as well as additional parameters specific to the function of the host 10. The host controller 22 may receive ventilator settings and other inputs from a clinician through the user interface 23 on the host 10. In certain embodiments, the parameters set at either user interface 21 or 23 may be received at either ventilator controller 20 or host controller 22 when the portable ventilator 2 is connected to the host. In various embodiments, communication between the ventilator controller 20 and the host controller 22 may be by a physical communication connection, or may be via any wireless protocol, such as Bluetooth, Bluetooth Low Energy (ELE), ANT, nearfield communication (NFC), or any other wireless communication protocol.

The portable ventilator includes at least one battery 43 or other power storage device configured to store and provide power to the ventilator 2. Thus, the ventilator 2 is portable and does not need to remain connected to an external power source. For example, the battery 43 may be rechargeable, such as when the ventilator 2 is connected to the host 10. In certain embodiments, the battery may be removable and configured to be removed and recharged on a separate charging system. As shown in FIG. 2A, the ventilator housing 222 of the ventilator 2 may be configured to facilitate easy removal and replacement of one or more batteries 43.

In certain embodiments, the host 10 may receive power from and/or supply power to the ventilator 2 and/or may charge the battery 43. In certain embodiments, the host may connect to a power source 18, such as a power outlet on a wall. In such embodiments, the host 10 may include a power connector 68 configured to deliver power to the ventilator 2 when it is connected to the host 10. In some embodiments, the host may further include a power controller, which may for example be integrated into the host controller 22, situated to control power delivered to the power connector 68. The power controller may distribute power throughout the host and to the portable ventilator 2 via power connector 68.

The ventilator controller 20 is configured to control various aspects of the portable ventilator 2. In certain embodiments, when the portable ventilator 2 is connected to the host 10, the host controller 22 may participate and/or take over control functions for the portable ventilator 2, including to control aspects of the ventilation drive 4 and/or the patient interface section 6. Referring to FIG. 5, the ventilation controller 20 and/or the host controller 22 may control various aspects of the ventilation drive 4, including pressure regulators, flow controller devices, valve actuators, and the blower module 26. Further, one or more of the ventilation controller 20 and/or the host controller 22 may receive information from sensors within the drive 4, such as $O_2$ sensors, pressure sensors, flow sensors, valve position sensors, etc. Additionally, the ventilation controller 20 and/or the host controller 22 may be configured to variously control the user interfaces 21, 23 on the ventilator 2 and/or the host 10.

Figure 2B:
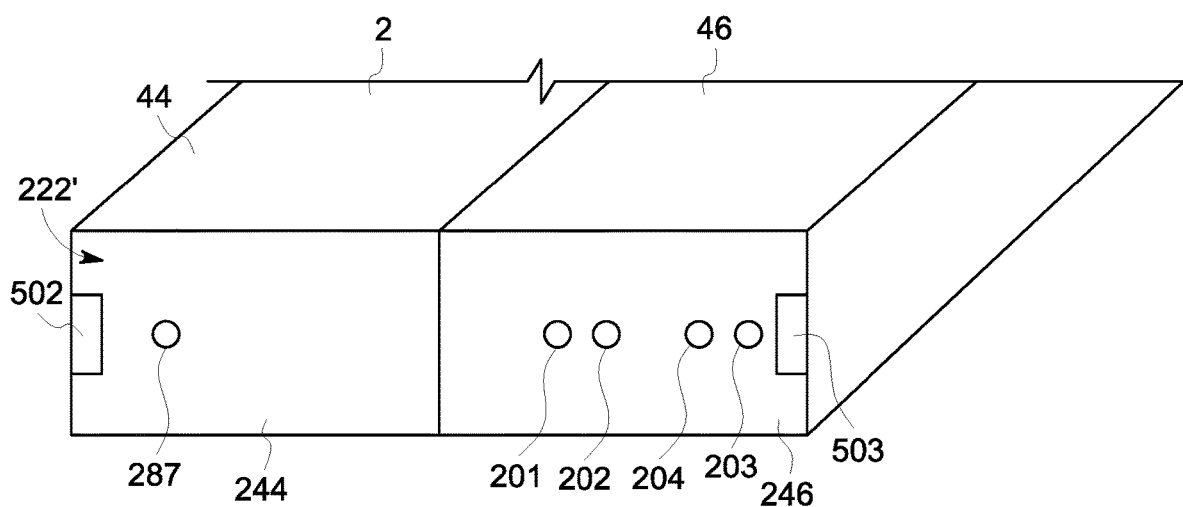

FIGS. 2A and 2B show an embodiment of a portable ventilator 2 detached from a host 10. The host includes a ventilator connection section 50 providing various ports and connectors, including the power connector 68 and pneumatic connection portions. Specifically, the ventilator connection section 50 includes a source connection port 87 configured to connect to ventilation gas port 287 on the ventilator 2 (see FIG. 2B). The host 10 includes a ventilation path portion 100 providing four ports 201-204 serving as inlets and/or outlets for inspiratory and/or expiratory gases to enter the ventilation path portion 100 of the host 10.

In the depicted example, the ventilation path portion 100 is configured to interface with the inspiratory path and expiratory path of the patient interface section 6. Further exemplary ventilation path portions, including inspiratory path portions 113b, 113c and expiratory path portions 115c and are provided herein, including at FIGS. 7 and 8. Connection ports 101 and 102 are configured to connect with inspiratory ports 201 and 202, respectively, to connect an inspiratory path portion 113b, 113c in the host 10 to the inspiratory path 60 in the patient interface section 6. Connection ports 103 and 104 on the host 10 connect to expiratory ports 203 and 204 on the ventilator to connect an expiratory path portion 115c of the host 10 within the patient interface section 6 to an expiratory path within the ventilation path portion 100 of the host 10.

Depending on the host type, various ventilator connection section 50 configurations may be provided, such as a ventilator connection section 50 only connecting one of the inspiratory or expiratory paths between the patient interface section 6 and the ventilation path portion 100 of the host 10. In other embodiments, no inspiratory or expiratory path connections are made between the ventilator 2 and the host 10, and thus the host 10 only provides a ventilation gas source connection between port 87 on the host and ventilation gas port 287 on the ventilator 2.

In the depicted embodiment, the ventilator connection section 50 provides a horizontal surface on which the ventilator 2 sits. A bottom side 222' of the ventilator housing 222 contacts a topside 48' of a host housing 48. In other embodiments, the ventilator connection section 50 may be oriented differently on the ventilator housing 222 and host housing 48. For example, the ventilator connection section 50 may be a vertical surface configured to connect to a vertical surface on the ventilator housing 222. In other embodiments, multiple connection sections and/or connection locations may be provided and the ventilator housing 222 and host housing 48 are correspondingly designed such that the multiple connections align when the ventilator 2 is connected to the host 10. The various ports are provided on the ventilator housing 222 and host housing 48 and positioned such that the ports on the ventilator 2 connect with a corresponding port on the host 10 when the ventilator 2 is vertically lowered onto the ventilator connection section 50.

The ventilator housing 222 includes a ventilation drive housing 44 and an interface housing 46. The ventilation drive housing 44 has a connection side 244 providing the ventilation gas port 287 that connects to the source connection port 87 on the host 10. The patient interface section 6 includes an interface housing having a connection end 246 providing ports 201 through 204 for inspiratory and expiratory path connections with the host 10.

In certain embodiments, connections means may be provided on the ventilator housing 222 and on the host housing 48 to secure the ventilator 2 onto the host 10. This may be important, particularly for portable hosts that may be moved, incur vibration and shock during transport, etc. In the embodiment at FIGS. 2A and 2B, each of the ventilator housing 222 and the host housing 48 have corresponding housing connectors that are configured to mate together to secure the ventilator 2 onto the host 10.

As shown in FIG. 2B, the ventilator housing 222 may have a first vent housing connector 502 and a second vent housing connector 503. Each of the vent housing connectors 502 and 503 are configured and positioned to connect to corresponding host housing connectors 512 and 513, respectively. Specifically, the first vent housing connector 502 connects to the first host housing connector 512 and the second vent housing connector 503 connects to the second host housing connector 513. In various embodiments, the vent housing connectors 502 503 and the host housing connectors 512 and 513 (referred to together as the "housing connectors") may be any type of connectors or connection formation that releasably connects the ventilator housing 222 and host housing 48. In certain examples, the housing connectors 502, 503, 512, 513 may be, for example, latches, hooks, thumbscrews.

A release means is also provided in order to release the vent housing connectors 502 and 503 from the host housing connectors 512, 513. In the depicted example, one or more release levers 501 may be positioned on the ventilator housing 222 and/or the host housing 48 and operatively connected and configured to release the connections when operated by a user. Thus, removal of the ventilator 2 from the host 10 may include operating the release levers 501, such as by turning or pulling up on the levers 501. The release levers 501 have internal connections or linkages within the housing 222 to operate or move the vent housing connectors 502 and 503 into a disconnection position that disengages from the host housing connectors 512 and 513. In other embodiments, other release mechanisms or means may be provided, such as buttons, screws, or the like. In still other embodiments, the housing connectors may be configured to provide a friction fit where no release mechanism is necessary and releasing the ventilator 2 from the host 10 is accomplished by pulling the ventilator housing 222 hard enough to overcome the friction force provided by the housing connectors 502, 503 and 512, 513. In various embodiments, different numbers and/or locations of housing connectors may be provided. A person of ordinary skill in the art will understand in view of the present disclosure that the location and number of housing connectors 502, 503, 512, and 513 are merely exemplary and other locations and numbers of connectors may be provided and such embodiments are within the scope of the present disclosure. In certain embodiments, a handle 224 may be connected to the housing 222 and configured to allow a clinician to easily lift and carry the ventilator 2. This facilitates easy movement and transport of the ventilator 2, as well as connection and disconnection from the hosts 10.

The ventilator housing 222 may comprise of two sections, the ventilation drive housing 44 and the interface housing 46. The ventilation drive housing 44 houses the ventilation drive 4, including the blower module 26 and other elements such as those described below with respect to FIG. 5. The interface housing 46 includes an inspiratory path 60 and an expiratory path 70 configured to guide the inspiratory and expiratory gas to and from the patient 16. The interface housing 46 and the ventilation drive housing 44 are configured to releasably connect together such that the patient interface section 6 can be removed from the drive 4. For example, the patient interface section 6 and interface housing 46 may be a cleanable, sterilizable, and/or autoclaveable portion. For example, the patient interface section may be comprised of polyphenylsulfone (PPSU) or other autoclaveable plastic material configured to withstand temperatures of 130 degrees C., or higher, for an extended period of time sufficient to provide sterilization. For example, the patient interface section 6 may an injection molded piece, such as a single continuous piece with smooth interior cavities to form the inspiratory path cavity and expiratory path cavity. In other embodiments, the patient interface section 6 may be formed of a machined metal, such as machined stainless steel. In still other embodiments, the patient interface section 6 may be a disposable unit that is intended for single-patient use. In such an embodiment, the patient interface section 6 may be comprised of a less expensive polymer material, for example, that does not need to be autoclaveable or otherwise sterilizable.

In certain embodiments, the ventilation drive housing 44 may include a drive housing connector 505 configured with and interface housing connector 506 on the interface housing 46. The drive housing connector 505 and interface housing connector 506 are configured to releasably mate so as to releasably connect the interface housings 46 and ventilation drive housing 44. The housing connectors 505 and 506 may be any of the above-listed connector types.

In certain embodiments, the expiratory path does not enter the ventilation drive housing 44 such that the ventilation drive 4 is not exposed in any significant way to any patient expiratory gas, other than perhaps at exterior connectors on the ventilation drive housing 44. Thus, the ventilation drive 4 and interior of the ventilation drive housing 44 are not exposed to the contaminants in the expiratory gases and may be cleanable by, for example, wiping down the exterior of the ventilation drive housing 44, particularly at the connection interface with the interface housing 46.

The ventilator 2 is configured to connect to one or more gas sources, including one or more portable gas sources 8. The ventilator 2 is portable, and thus may also be referred to herein as "portable ventilator". In certain embodiments, the portable ventilator 2 may also be configured to connect directly to wall gas via one or more wall gas lines 158, and/or other gas sources including gas cylinders. In one embodiment, the portable ventilator 2 may include multiple gas source connections 29a and 29b, as shown in FIG. 2A, to connect to different gas source types. For example, the portable ventilator 2 may be configured to connect to an oxygen tank, as well as to wall gas, such as a low-pressure wall gas source. In the depicted example, wall gas line 158 connects to the source connection 29a to provide a low-pressure gas source. For example, the wall gas line 158 may be connected to a pressure regulator providing low-pressure oxygen at a pressure of 100 kilopascals (kPa) or less, from a wall gas source. Such low-pressure oxygen arrangements are known in the art.

Figure 3:
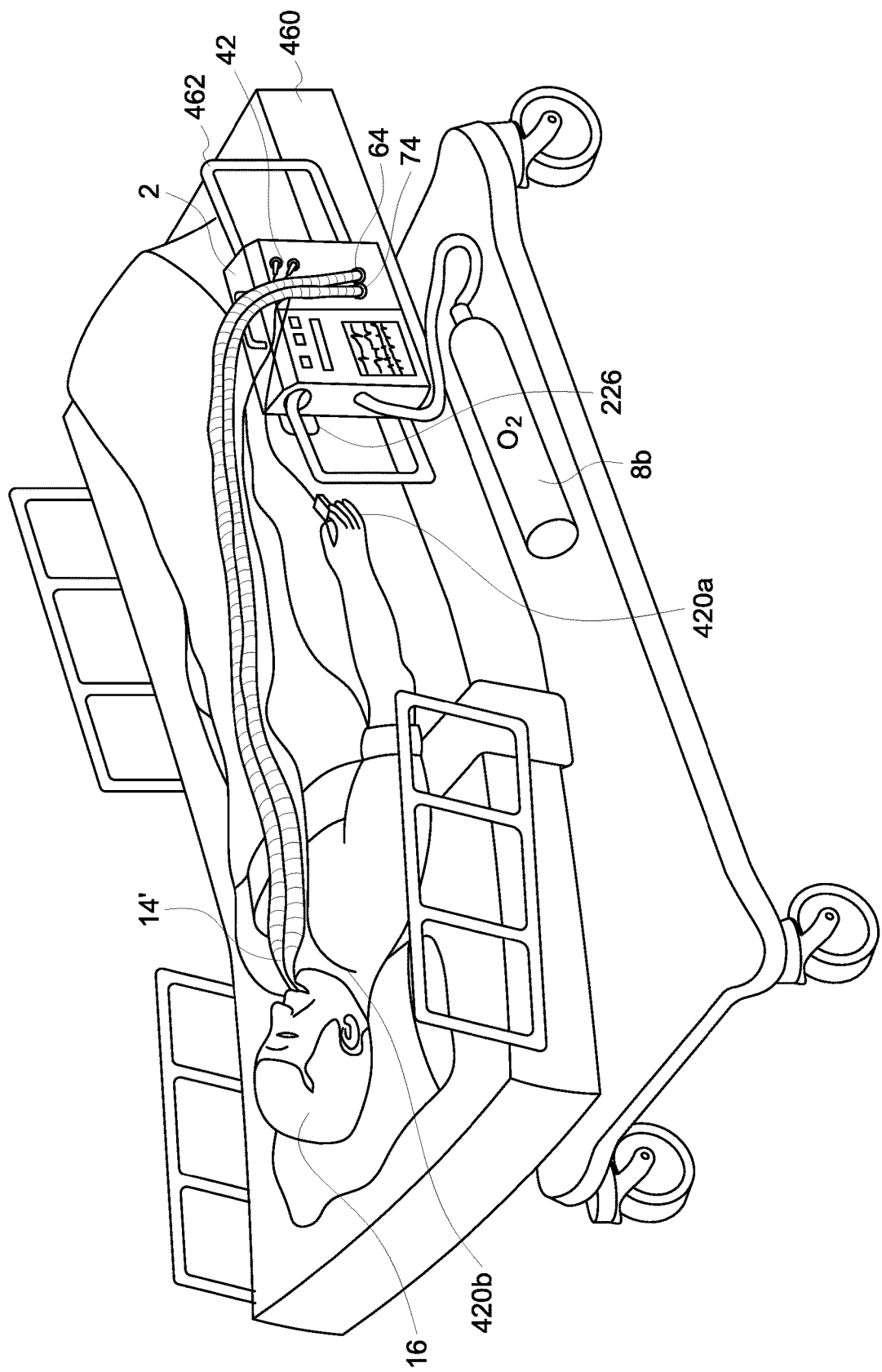
FIG. 3 depicts an exemplary embodiment of a portable ventilator in use on a patient during transport.

The ventilator 2 may also be configured to connect to a higher pressure gas source at connection 29b. The portable gas source 8 may be, for example, an oxygen tank, such as having a pressure of 242-648 kPa (35-94 psig). FIG. 3 illustrates one such embodiment where a portable gas source 8b is an oxygen tank connected to the portable ventilator 2 and transported therewith. This configuration demonstrates a portable ventilator 2 utilized on its own during patient transport, such as where the patient is being transported from the OR to the ICU or vice versa. The portable ventilator 2 can be utilized to ventilate the patient for an extended period of time provided that the batteries 43 or other power source are exchanged or wall power is utilized and the portable gas source 8b is sufficiently changed or swapped. Thus, use of the portable ventilator 2 is not only confined to patient transport or short utilization periods because the ventilator 2 provides full ventilation functionality for normal continued ventilation support.

In the depicted example, the patient 16 is intubated and the patient connection 14' is an endotracheal tube. The endotracheal tube patient connection 14' is connected to the inspiratory connection port 64 and the expiratory connection port 74 on the ventilator 2, and particularly on the interface housing 46 on the patient interface section 6. Patient monitors 420 are also operatively connected to the patient 16 to provide patient monitoring data to the ventilator 2. In the depicted example, an $SpO_2$ patient monitor 420a and an ECG patient monitor 420b, and respective sensors therefore, are each connected to respective patient monitoring ports 42 on the ventilator housing 222. Thereby, patient physiological data is provided to the ventilator 2, which may be used by the controller 20 for controlling ventilation to the patient as well as for general patient monitoring and alarming. Patient physiological information based on the monitoring data may be displayed on the user interface section 21b, such as on the ventilator display 21c.

In certain embodiments, the portable ventilator 2 may be configured to hook or connect to the side of the patient's bed 460. For example, the ventilator housing 222 may comprise hooks 226 or other attachment means for attaching the portable ventilator 2 to a side rail 462 of the patient's bed 460. A person of ordinary skill in the art will understand in view of the present disclosure that other mounting means and locations are within the scope of the present disclosure.

Figure 4A:
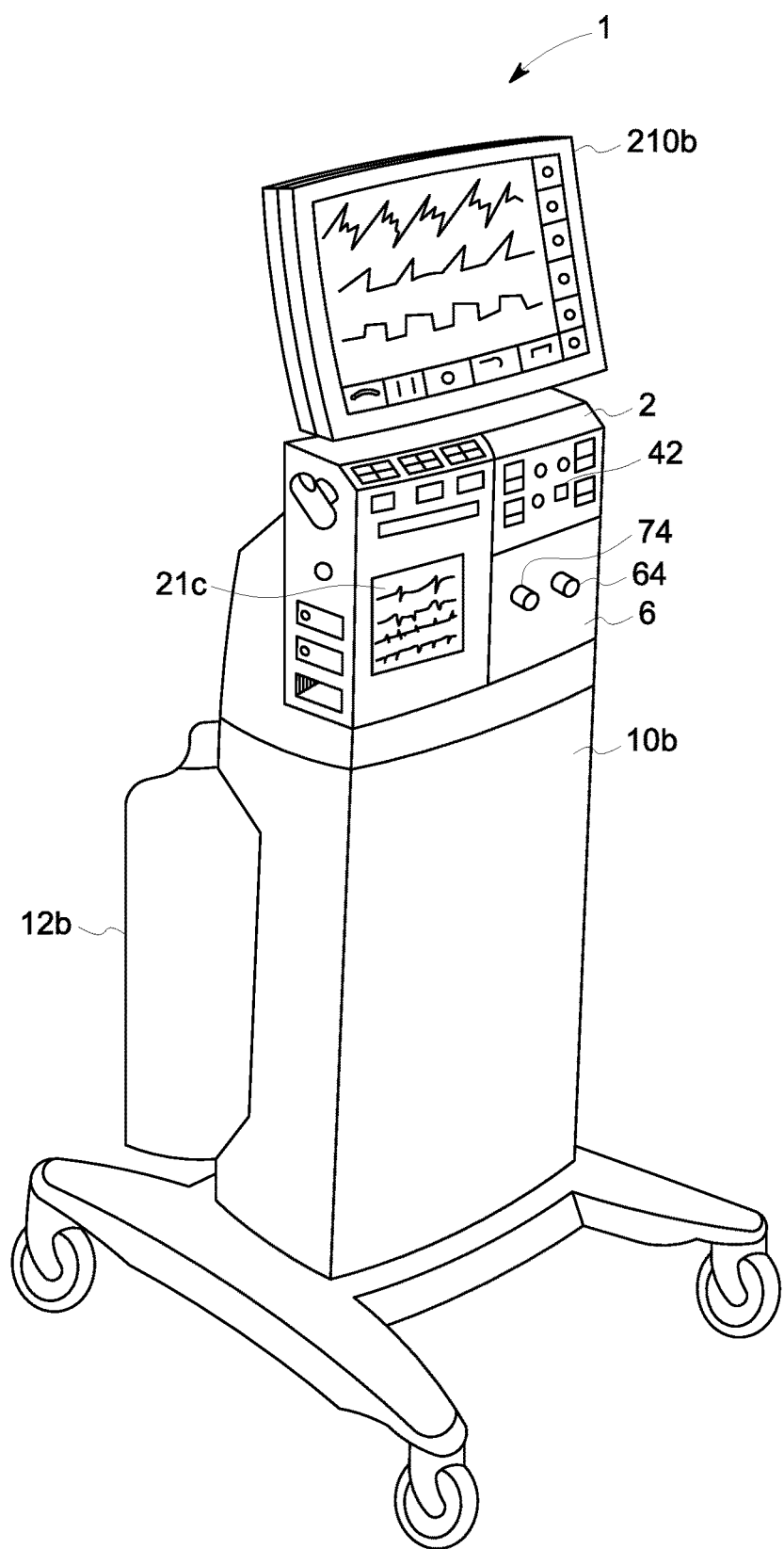
FIGS. 4A and 4B depict an exemplary embodiment of a ventilator system incorporating the portable ventilator of FIGS. 2-3.
Figure 4B:
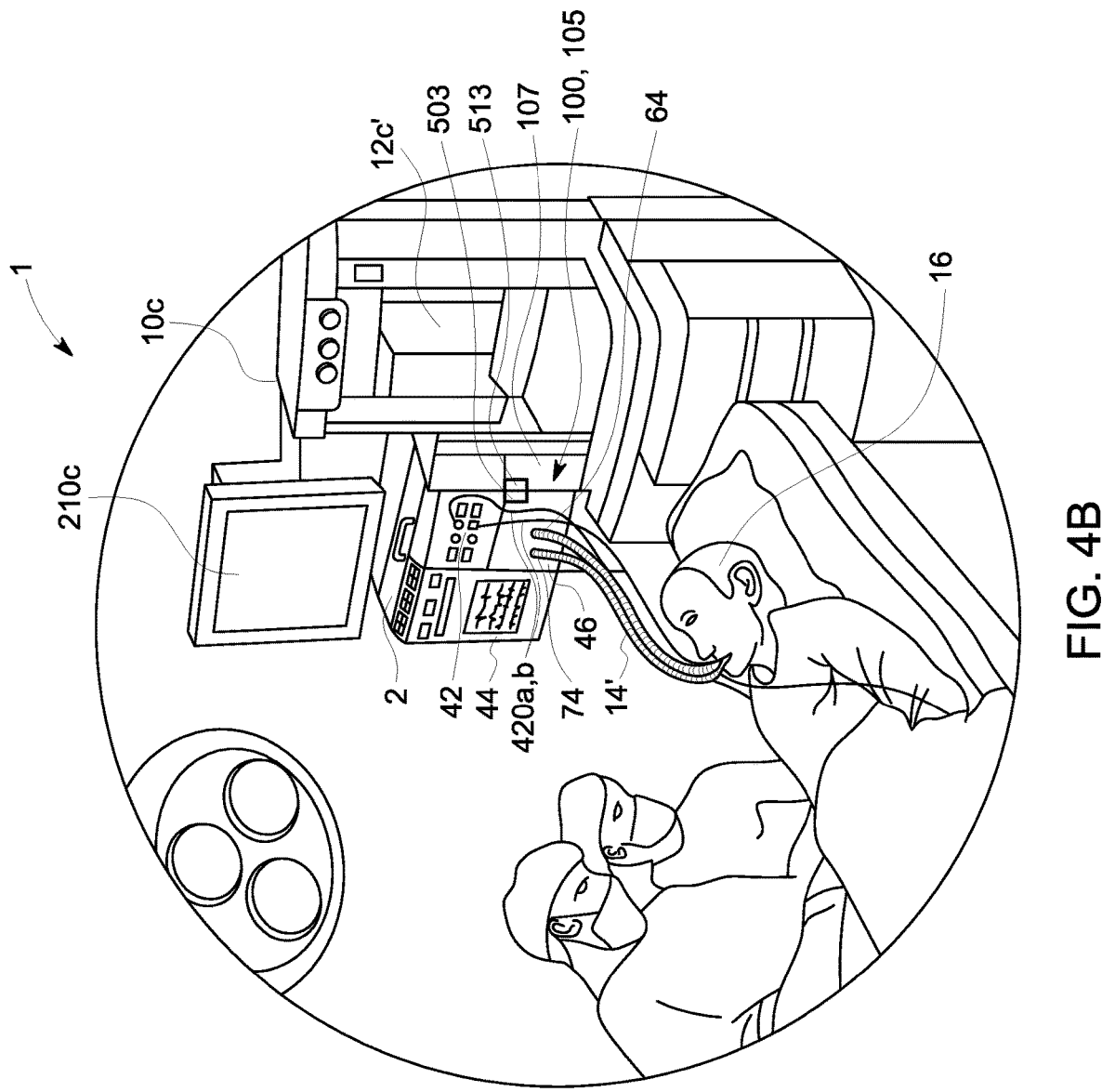

The portable ventilator 2 is configured to connect to multiple different hosts 10, one at a time. FIGS. 4A and 4B depict the portable ventilator 2 of FIGS. 2 and 3 connected to different hosts 10. FIG. 4A shows the portable ventilator 2 connected to an ICU host 10b providing on/off valves, such as P01 valves described below with respect to FIG. 7. The ICU host 10b includes a host gas source 12b, such as an oxygen tank, which in some embodiments may be a larger oxygen tank then the portable gas source 8b. In other embodiments, the ICU host 10b may be connected to a wall gas source to serve as the host gas source 12b.

The patient 16 remains connected to the connection ports 64 and 74 when the ventilator 2 is connected to the host 10b. No disconnection of the patient is required when transferring and the ventilator 2 is configured to seamlessly switch from providing inspiratory gas from the portable gas source 8b to providing inspiratory gas to the patient from the host gas source 12b. Likewise, the patient monitors 420 remain connected to the patient monitoring ports 42 and thus no change or interruption in patient monitoring is required for connection to the host 10b.

In certain embodiments, the ICU host 10b may include a host display 210b. In some embodiments, the host display 210b may be configured to repeat the information displayed on the ventilator display 21c. In other embodiments, the host display 210b may display different or additional parameters or information. The host display 210b may serve as the user interface 23 for the host 10b, such as to provide control parameters for controlling the ventilation path portion 100 and/or other functions of the ICU host 10b.

FIG. 4B depicts a ventilation system 1 configuration where the portable ventilator 2 is connected to an anesthesia host 10c. Again, the patient 16 remains connected to and continually ventilated and monitored by the ventilator 2, including continued connection to connection ports 64, and 74 and to the patient monitoring ports 42. The anesthesia host 10c provides a host gas source 12c, which is typically wall gas but may include a cylinder or other gas container and may further include an anesthesia gas source 12c'. The anesthesia host 10c includes a ventilation path portion 100 that comprises a circle breathing system 105. As exemplified in the embodiment at FIG. 8, the circle breathing system 105 includes a circle drive unit 114, such as a plenum and is configured to connect to both the inspiratory and expiratory paths to provide anesthesia ventilation to the patient. Various circle system configurations are known to those with skill in the art and are within the scope of the present disclosure.

In certain embodiments, the circle breathing system 105 is housed in a circle section housing 107 which may be removable from the anesthesia host 10c. For example, the circle section housing 107 may be releasably connected to a housing of the host gas delivery section 95. In certain embodiments, the interface housing 46 and the circle section housing 107 releasably connect. As illustrated in FIG. 4B, the circle section housing 107 is adjacent and aligned with the interface housing 46. A vent housing connector on the interface housing 46 is configured to releasably connect to a host housing connector on the host, which in some embodiments may be preferably located on the circle section housing 107. In the depicted example, ventilation housing connector 503 is configured to connect to the host housing connector 513.

In certain embodiments, the interface housing 46 can be released and disconnected from the ventilation drive housing 44 at the same time that the circle section housing 107 is released and disconnected from the host 10c such that they are removed together as a connected unit. The two housings, including interface housing 46 and circle section housing 107, may then be cleaned, disinfected, and sterilized, which may be completed on the connected unit or the interface housing 46 and the circle section housing 107 may be disconnected prior to cleaning and/or sterilization. For example, the interface housing 46 and the circle section housing 107 may be configured to fit together as a clam shell and, once removed from the ventilator 2 and the host 10c, then released from one another for cleaning, disinfection, and sterilization. In certain embodiments, the circle section housing 107 may be an injection molded or machined piece, such as manufactured in the same way as the interface housing 46, examples of which are described above.

In certain embodiments, one or more valves may be configured to control flow of ventilation gas within the portable ventilator 2 and/or to and from the host 10. In the example at FIG. 5, the portable ventilator 2 includes two sets of diverter valves 61-62 and 71-72 controlling the inspiratory and expiratory path connections such that they either remain within the portable ventilator only or are diverted to the inspiratory path portion, the expiratory path portion, or both of the host. FIG. 5 is a pneumatic diagram demonstrating an exemplary embodiment of a portable ventilator 2 including a ventilation drive 4 that connects to a host gas delivery section 95 so as to receive inspiratory gas from a host gas source 12. The ventilator 2 includes a patient interface section 6 that connects to multiple different host types providing differing ventilation path portions 100 and specialized ventilation functionality.

The sets of diverter valves include a set of inspiratory diverter valves 61 and 62 configured to control the inspiratory path 60, and a set of expiratory diverter valves 71 and 72 configured to control the expiratory path 70. Each set of valves 61 and 62, 71 and 72, may be configured to open or close simultaneously and together. For instance, the inspiratory diverter valves 61 and 62 may be configured such that either both are open or both are closed. Similarly, expiratory diverter valves 71 and 72 may be jointly actuated and configured such that both are open and closed simultaneously.

In certain embodiments, each of the diverter valves 61, 62, 71, 72 may be two-position three-way valves, and may be normally closed-type valves configured to be close in an unactuated, unpowered resting state and to open when the portable ventilator connects to the host 10. Thus, when the inspiratory diverter valves 61, 62 are closed, the inspiratory pathway 60 is maintained within the portable ventilator 2. Thus, the inspiratory path flows along path portion 60a between the valves 61 and 62. When the inspiratory diverter valves 61, 62 are open, the inspiratory pathway is diverted into the host 10 along path section 60b (traveling back from the host up path portion 60c). Similarly, when the expiratory diverter valves 71, 72 are no actuated, and thus closed, the expiratory path 70 is maintained within the portable ventilator 2 flowing between valves along path portion 70a. When expiratory diverter valves 71, 72 are forced open on connection to certain types of hosts, the expiratory gas is diverted along path portion 70b into the host 10 (and returns along path portion 70c). The diverter valves 61, 62, 71, 72 may be mechanically actuated valves, such as actuated by the mechanical force of connecting the portable ventilator 2 to the host 10, or electrically actuated valves, such as solenoids that are electrically configured to actuate the valves when the portable ventilator 2 is connected to the host 10.

The portable ventilator 2 may further include one or more host source connection valve 28 configured to control connection of a host gas source 12 to the ventilation drive 4 such that ventilation gas can be provided therefrom. The host source connection valve 28 may be, for example, a two-way two-position valve. It may be a normally closed-type valve, and may be a mechanically actuated or electromechanically actuated valve. When the host source connection valve 28 is in the default closed position, such as when the portable ventilator 2 is not connected to a host 10, then no gas flow is provided from the host gas source 12. Conversely, when the host source connection valve 28 is opened, such as electrically or mechanically actuated, then gas is permitted to flow from the host gas source 12 into the vent drive 4. Likewise, if the host gas source 12 gets depleted or malfunctions then the portable gas source 8b is automatically utilized. Thus, input gases may be driven by the ventilation drive 4 to the patient from either a portable gas source 8 connected directly to the ventilation drive 4 or the host gas source 12 connected through the host 10 to the ventilation drive 4.

In the depicted embodiment, the portable ventilator 2 is configured to receive ventilation gas from either of two gas sources 8, including low-pressure oxygen source 8a and high-pressure portable gas source 8b. For example, the low-pressure oxygen source 8a may be a lo-pressure regulated wall gas source, such as configured to provide 15 lpm and a pressure of 100 kPa, or less. Alternatively, the low-pressure gas source may be a small $O_2$ cylinder. The high-pressure oxygen is a higher-pressure gas source than the low-pressure source, such as ranging between 242-648 kPa (35-94 psi). When a high-pressure portable gas source 8b (such as an oxygen source) is connected, the portable gas source input valve 34a, such as a check valve, receives a higher pressure on the downstream side and prevents flow from the low-pressure gas source 8a. However, if no high-pressure portable gas source 8b is connected or the higher-pressure source is depleted, then gas may be automatically provided by the low-pressure oxygen source 8a and gas source input valve 34a forced open.

If gas is provided from the high-pressure portable gas source 8b, which is connected to the portable source connection 29b and provides gas to the input gas path 30b, the input gas is filtered at filter 32b. Input pressure is measured by pressure sensor 33 and the input gas passes through portable gas source input valve 34b and provided to the pressure regulator 36. Pressure regulator 36 is configured to regulate the delivery pressure of ventilation gas from the portable gas source 8b. For example, the pressure regulator 36 may be configured to provide a delivery pressure of ventilation gas from the portable gas source of 172 kPa (25 psi). The pressure regulated gas is then provided to the flow controller 40, such as a flow control valve. Pressure sensor 39 is configured to measure the delivery pressure of gas to the flow controller. A test port with a plug and check valve may be provided along the input gas path 30bc delivering gas to the flow controller 40.

In certain embodiments, the host gas is delivered at a higher pressure than the gas from the portable gas source and the ventilation drive 4 is configured to provide gas only from the highest-pressure source. FIG. 5 exemplifies such an embodiment, where gas source input valves 34a and 34b in the input gas paths 30a and 30b provide gas from one of the gas sources, including the low-pressure oxygen source 8a and portable gas source 8b (referred to collectively as gas sources 8a and 8b), when the portable ventilator 2 is not connected to any host 10. When the portable ventilator 2 is connected to a host 10, and thus to a host gas source 12, the gas source input valves 34a and 34b close to prevent any backflow and otherwise shut off the lines connecting to the gas sources 8a and 8b. For example, the gas source input valves 34a and 34b may each be a check valve. When the host gas source connection valve 28 is closed, and thus the portable ventilator 2 is disconnected from the host, the gas source input valve 34a or 34b seeing the highest pressure between the gas path 30a and the gas path 30b will open. Thus, gas source is provided from just one of the gas sources 8a, 8b, or alternatively the host source 12, which is the one gas source providing the highest pressure.

Flow sensor 41 senses the flow rate outputted by the flow controller 40, such as a flow control valve or other device for controlling gas flow, along gas flow path 45 provided to the blower module 26. The blower module 26 is controllable to provide cyclical inspiratory and expiratory pressure as required for the patient. The blower 56 is controlled, such as by ventilator controller 20 to provide inspiratory gas flow at an appropriate inspiratory gas flow rate and to significantly reduce the airflow during the expiratory portion of the patient's ventilation cycle. Similarly, the flow controller 40 is configured to control flow of the ventilation gas to provide the inspiratory flow and to significantly reduce or turn off the ventilation gas flow during the expiratory phase. The blower 56 may be configured to intake air from atmosphere through the air intake port 9 along input path 30d. The atmospheric air is filtered by the inlet filter 47. The blower 56 thus can circulate ventilation gas into the patient interface section 6 provided by either the low-pressure gas source 8a, or low-pressure oxygen source, the high pressure oxygen source 8b and/or from atmosphere. Output flow from the blower is sensed by the flow sensor 47, which senses the total output flow from all gas sources provided by the blower 56. An $O_2$ sensor 49 may be configured to sense the oxygen present in the output flow, which is provided in the inspiratory path 60' to the patient interface section 6.

A check valve 54 may be provided at the interface between the ventilation drive 4 and the patient interface section 6. Check valve 54 prevents backflow of gases back into the drive 4. Inspiratory gases are provided to the patient on inspiratory path 60. As described above, depending on the position of the inspiratory diverter valves 61 and 62, the inspiratory path may travel directly from the drive connection to the patient connection 14, or it may be diverted into a gas path section in the host 10.

For the exhalation gas cycle, expiratory gases travel from the patient, through the patient connection 14 to the expiratory connection port 74 and into the patient interface section 6. The expiratory gases follow the expiratory path 70 through the patient interface section 6, where the expiratory gases are expelled out of the portable ventilator 2. If the expiratory diverter valves 71 and 72 are closed, then gas travels along path 70a between the diverter valves and continues along the expiratory path 70 within the patient interface section 6. If the expiratory diverter valves are open, then the gas is diverted to the host 10. This example utilizes normally closed-type valves, in other examples, normally open-type valves may be utilized and the configuration may be adjusted accordingly, as will be understood by a person of ordinary skill in the art in view of the present disclosure. When the expiratory diverter valves 71 and 72 are positioned to divert flow into the host 10, the expiratory gas travels down the path portion 70b into the host. Where the host provides a circle system, such as exemplified at FIG. 8, the gas may be returned from the host to the patient interface section 6 at path 70c to continue along expiratory path 70. Expiratory gas flows through the exhalation valve 76, which is actuated by actuator 76a. During the exhalation portion of the ventilation cycle, the exhalation valve 76 is positioned to open the flow path to the expiratory port 78. An exhalation flow sensor 77 may be positioned and configured to measure the flow rate of the exhalation gas exiting the expiratory port 78. When the portable ventilator 2 is not connected to any host, the expiratory port 78 vents the exhalation gases to atmosphere. In certain embodiments, a filter, scrubber, sterilizer, scavenging system, or some other gas processing system may be positioned at the expiratory port 78 to filter or sterilize the exhalation gases. In certain embodiments, a valve, such as a check valve, may be positioned at the expiratory port 78 so as to only allow output flow and prevent any intake at the exhalation port.

Safety valve 66 and respective valve control actuator 66a also assist in actuating and controlling the valve 66 state. Valve 66 may comprise a flexible membrane, the movement of which is controlled by the ventilation drive using the actuator 66a. Safety valve 66 acts as a release valve if airway pressure becomes too high, thereby preventing overly high lung pressure of the patient. In various embodiments, safety valve 66 may be configured to vent gas to atmosphere or to vent to a scavenging system. In certain embodiments, the valve 66 may vent gas to atmosphere when not connected to any host and/or when not connected to a host providing a scavenging system.

Figure 6:
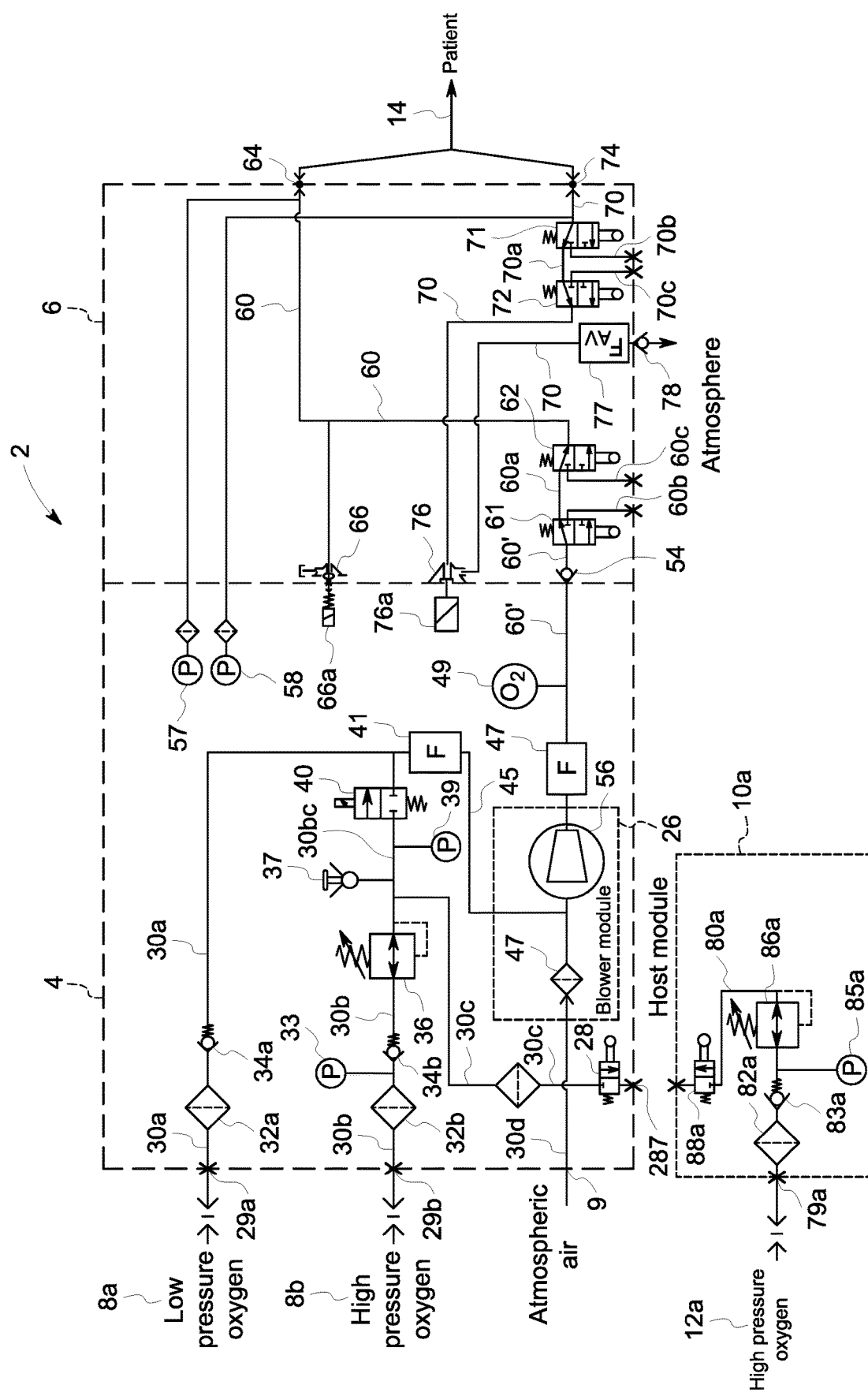
FIGS. 6-8 are system diagrams showing the ventilator embodiment of FIG. 5 in cooperation with various hosts.
Figure 7:
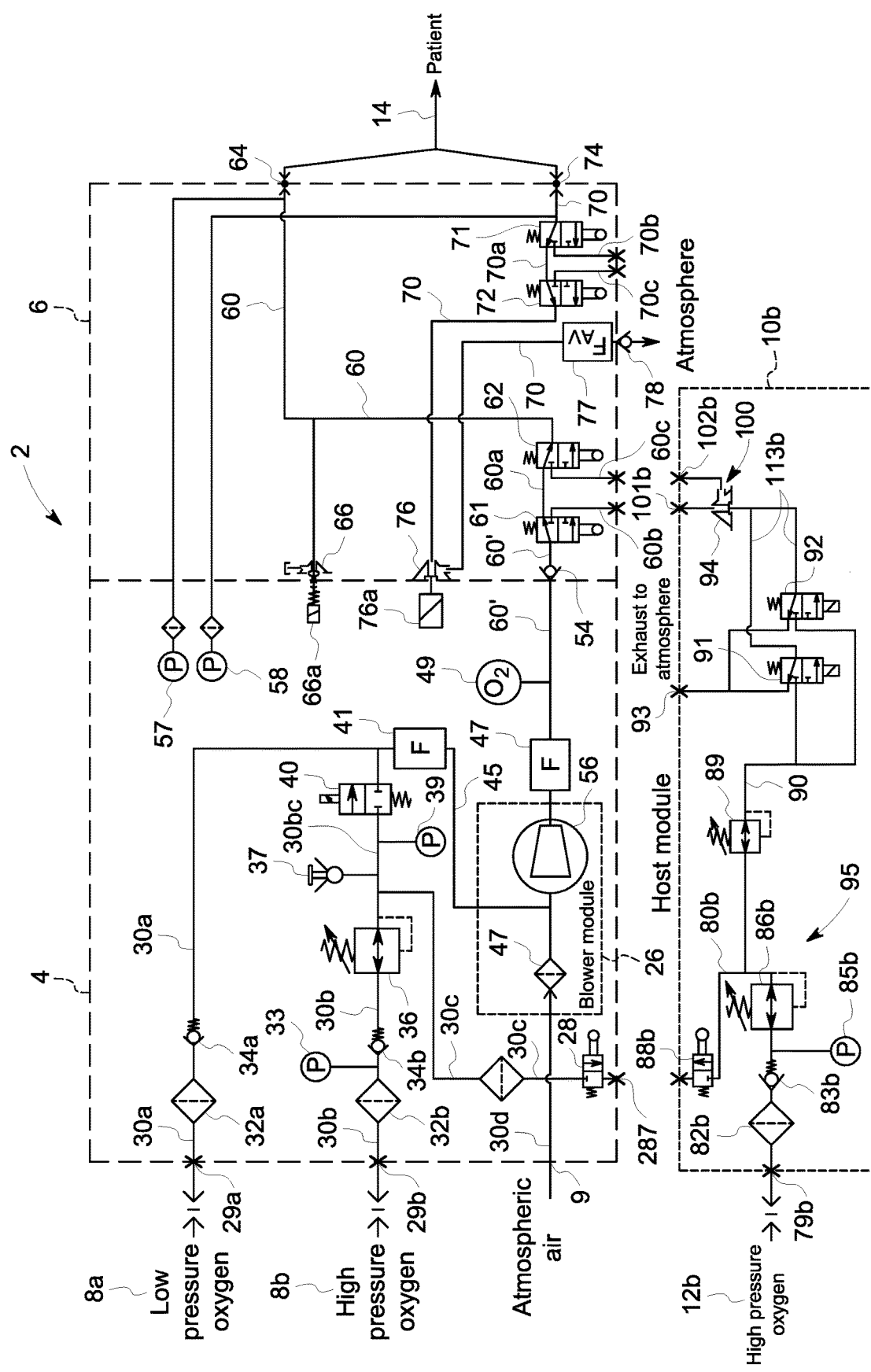
Figure 8:
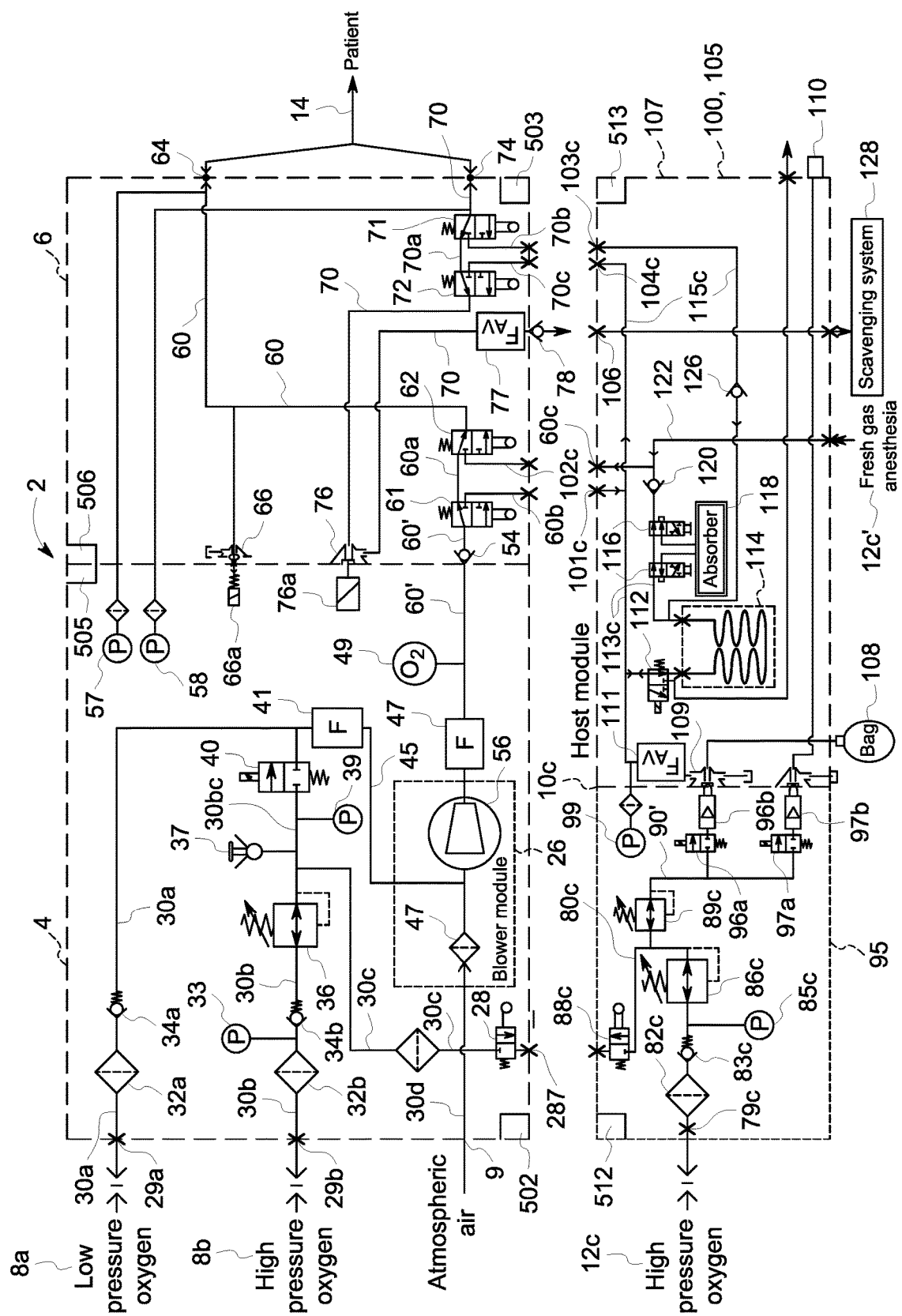

FIGS. 6-8 depict various hosts and the connection between the host and the portable ventilator 2. FIG. 6 depicts a host providing a host gas source 12a, which may be a larger oxygen cylinder or other oxygen reserve, or may be wall gas. For example, the host source may be stored and provided at 242-648 kPa (35-94 psig). In this example, the host 10a only provides gas to the ventilation drive 4 and does not connect to the patient interface section 6. For example, the host module 10a, joined with the portable ventilator 2, may provide a simple ICU ventilator, with the host module 10a providing a host gas source that is larger than the portable gas source 8. The host gas source 12a connects to the host module 10a at port 79a and is filtered at filter 82a. The ventilation gas from the host gas source 12a then travels through check valve 83a and is provided to the pressure regulator 86a. Pressure sensor 85a measures the input pressure to the pressure regulator. The gas then flows along the host input path 80a to the ventilation drive 4.

The pressure regulator 86a can be configured to provide a higher delivery pressure than the regulator 36 in the ventilation drive 4. Thereby, when the portable ventilator 2 is connected to the host, ventilation gas from the higher-pressure host will be provided by the ventilation drive to the patient. For example, the host pressure regulator 86a may be configured to provide 28 psi, which is greater than the exemplary 25 psi of the pressure regulator along the portable gas input path 30b. The ventilator source connection valve 88a may be configured to open when the portable ventilator 2 is connected to the host 10a. For example, the ventilator source connection valve 88a may be configured to interact and/or cooperate with the host source connection valve 28 such that both valves open, either via mechanical or electrical actuation, when the portable ventilator 2 is properly connected to the host 10a.

FIG. 7 exemplifies another host type, which in the depicted example is an ICU host 10b allowing additional functionality to turn on and off the inspiratory flow, thus enabling a maneuver to measure patient inspiratory drive. In this example, the host 10b provides a host gas source 12b that provides higher pressure gas as described above with respect to host 10a. In the depicted exemplary embodiment, the port 79b, filter 82b, check valve 83b, pressure sensor 85b, pressure regulator 86b, and ventilator source connection valve 88b all operate similarly to the correlating features in FIG. 6 and thus provide ventilation gas from the host gas source 12b to the ventilation drive along path 80b. In addition, the host module 10b includes a ventilation path portion 100 connects downstream in the inspiratory path. In the depicted embodiment, the ventilation path portion 100 includes at least one on/off valve 94 configured to enable a "P01" maneuver to measure patient inspiratory drive such as to perform a negative inspiratory force measurement from the patient. The host 10b connects to the inspiratory path 60 at path sections 60b and 60c via connection ports 101b and 102b.

In certain embodiments, connection port 101b may be configured to mechanically actuate the diverter valve 61 and connection port 102b may be configured to mechanically actuate the diverter valve 62 in the portable ventilator 2. Referring also to the embodiment depicted at FIG. 2A, each connection port 101 and 102 may include an actuator 141 and 142 on the host housing 48 that is configured to mechanically actuate the valve 61 and 62, such as to move the valve flap 161, 162 thereof (see also FIG. 9C). In the example shown at FIG. 2A, the actuators 141 and 142 are upward projections that are adjacent to or otherwise associated with each connection port 101 and 102 and are configured to extend into the ports 201 and 202 on the ventilator housing 222 so as to push open the valves 61 and 62. Thereby, mechanical connection of the portable ventilator 2 to the host 10b mechanically actuates opening of the valves 61 and 62 that permit inspiratory gas flow to the inspiratory path portion 113b of host 10b. In other embodiments, such actuation may be electrical and the valves 61 and 62 may be electromechanical valves.

A pressure regulator 89 is positioned on flow path 90. For example, the pressure regulator may be configured to provide 350 mbar of pressure. The flow path 90 travels to an inspiratory on/off valve 94, or a P.01 valve. When the inspiratory on/off valve 94, or P.01 valve, is open, gas travels along path section 60b of the patient interface section 6 through the on/off valve 94 to connector 102b and further to patient interface section 6 channel 60c. The on/off valve 94 may be a pneumatically driven valve comprising a flexible membrane separating the inspiration gas path between connection ports 101b and 102b from the pneumatic drive pressure channel 113b. The valve closes the inspiration channel between connection ports 101b and 102b when actuated. Actuation occurs by electrical activation of the solenoid valves 91 and 92, which allows the regulator 89 outlet pressure to drive on the on/off valve 94. When the pressure measurement at the on/off valve 94 is passed, the valves 91 and 92 are de-activated, which allows the pilot drive pressure from the valve 94 to be exhausted to atmosphere, allowing the on/off valve 94 to open the path between connection ports 101b and 102b. This opening may occur due to the elasticity of the flexible membrane or with aid of a spring biasing the membrane to keep the inspiration gas path open.

FIG. 8 depicts another host type, which in this depicted example is an anesthesia host 10c. The anesthesia host 10c includes a host gas delivery section 95 and a circle breathing system 105. The gas host gas delivery section 95 connects to a host gas source 12c that provides higher pressure gas as described above with respect to host 10a. The port 79c, filter 82c, check valve 83c, pressure sensor 85c, pressure regulator 86c, and ventilator source connection valve all 88c may all operate similarly to the correlating features described above with respect to FIG. 6, and thus provide ventilation gas from the anesthesia source 12c' to the ventilation drive along path 80c. In addition, the anesthesia host 10c connects downstream in the inspiratory path 60 to provide a circle system for providing anesthetic agent and corresponding ventilation for supporting anesthesia delivery to the patient. In conjunction with the circle breathing system, the host gas delivery section 95 of the anesthesia host 10c may include additional elements to deliver gas to the bag 108 through the bag on/off valve 96a and the bag switch 96b. Thereby, the bag 108 can be utilized to drive gas to and from the patient interface section 6, including through the circle breathing system 105. Additionally, certain embodiments of the host gas delivery section 95 may include a test port on/off valve 97a and a test port switch 97b that control gas flow to a test port 110.

The circle breathing system 105 of the anesthesia host 10c connects to the inspiratory path at path sections 60b and 60c. Inspiratory gas is received to the host from path section 60b which is delivered to and circulated through the circle system. Anesthesia breathing gas is provided back to the patent interface section 6 through path section 60c for delivery to the patient. The anesthesia host 10c includes connection ports 101c and 102c that facilitate connection of the inspiratory path sections 60b and 60c to the inspiratory path portion 113c of the host 10c. The inspiratory path portion 113c is the gas path between the connection ports 101c and 102c, which includes the circle drive unit 114 and the $CO_2$ absorber 118.

In certain embodiments, the connection port 101c and 102c may be configured to mechanically actuate the respective diverter valves 61 and 62, as described above. In other embodiments, the diverter valves 61 and 62 may be electromechanical valves that are electrically actuated upon connection of the portable ventilator 2 to the anesthesia host 10 and once proper connection is verified. For example, such electrical actuation may be based on pressure and/or electrical connection sensing to verify that the pneumatic and electrical connections are proper.

In an inspiratory cycle, gas flows from the ventilation drive 4 to connection port 101c to the flow selector valve 112 and into the circle drive unit 114. The circle drive unit 114 may be, for example, a plenum as illustrated in the embodiment. In another example, the circle drive unit may involve a bellows configured to drive gas through the circle breathing system 105. Gas is driven by the circle drive unit 114 through the set of valves 116, which divert the gas through the $CO_2$ absorber 118 along the path to the inspiratory valve 120. In the depicted example, the inspiratory valve 120 is a check valve. Gas that passes through the inspiratory valve 120 combines with gas from anesthetic gas source 12c', which includes fresh gas and anesthetic agent, such as vaporized anesthetic drugs and other anesthetic gases. The anesthetic gas and fresh gas mixture are conveyed along the gas flow path 122, combine with the inspiratory gas conveyed through inspiratory valve 120, and then exit the circle breathing system 105 of the host 10c at connection port 102c, where it is delivered to the inspiratory path section 60c and eventually to the patient.

On the expiratory cycle, gas is delivered from expiratory flow path portion 70b through the connection port 103c and into the circle breathing system. Similar to connection ports 101c and 102c, connections ports 103c and 104c connect to the gas flow paths of the portable ventilator 2 and may facilitate electrical and/or mechanical valve actuation in order to facilitate gas flow between the flow path within the patient interface section 6 and the circle breathing system 105. The connection port 103c connects to the expiratory path portion 70b following diverter valve 71 and is configured to facilitate input of the expiratory gases from the patient interface section 6 into circle breathing system in the host 10c. The connection port 104c connects to the expiratory flow path portion 70c which delivers gas to diverter valve 72 and through the exhalation path 70. Expiratory flow that enters through connection port 103 travels through the expiratory valve 126, which may be a check valve, to the drive unit 114 and flow selector valve 112 to port 104c that connects to expiratory path portion 70c in the patient interface section 6. Connection port 106 may be configured to connect to the expiratory port 78 of the portable ventilator 2 to provide the expiratory gases to a scavenging system 128. The circle breathing system 105 may also include a bag 108 and corresponding valve 109 to allow gas to be drive though the circle breathing system via a manually compressible bag, as is well known in the art. A bag flow sensor 111 may be provided along the flow path driven by the bag 108 in order to sense the driven gas flow through the bag valve 109.

Diverter valves 71 and 72 may be mechanically or electrically actuated when the ventilator 2 is connected to certain hosts, such as anesthesia host 10c, that interface with the expiratory path. In certain embodiments, connection ports 103 and 104 may have associated actuators 143 and 144 configured to mechanically actuate, or open, the valves 71 and 72. As described above with respect to the inspiratory diverter valves 71 and 72, in one example the actuators 143, and 144 may be projections configured to push open the valve flaps 171, 172 when the ventilator is seated onto the host 10c.

Figure 9A:
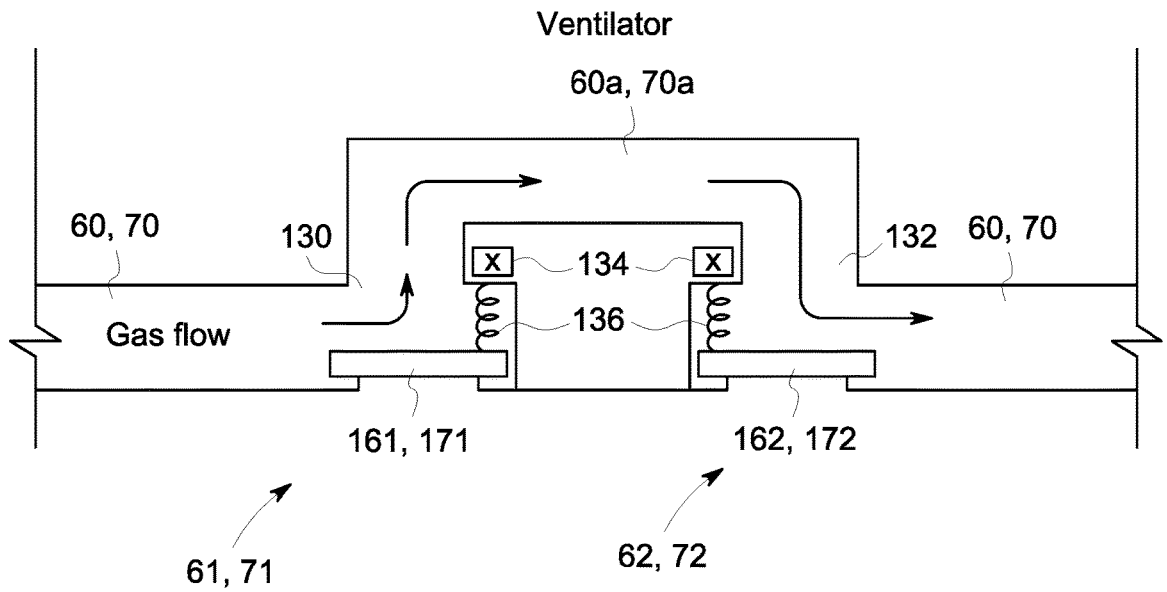
FIG. 9A depicts an exemplary embodiment of a set of diverter valves in a ventilator in a first position wherein the portable ventilator is not connected to a host.
Figure 9B:
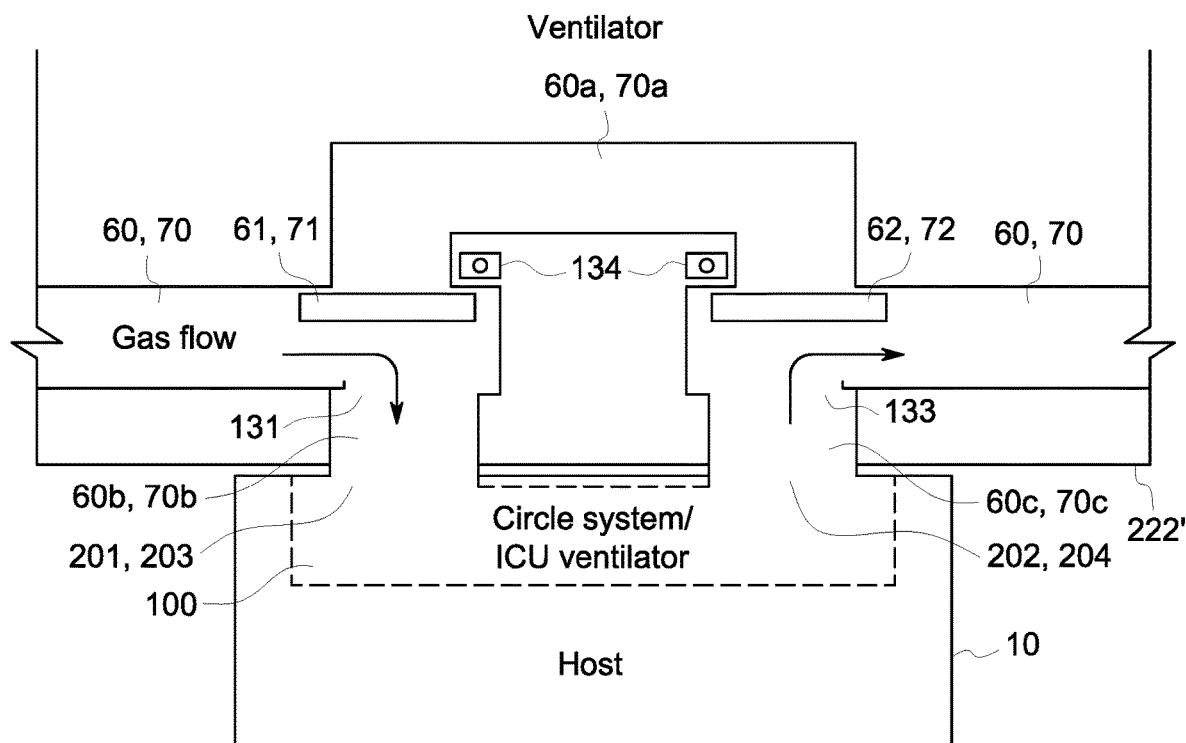
FIG. 9B depicts the set of diverter valves in FIG. 9A in a second position where the ventilator is connected to a host.

FIGS. 9A and 9B depict an exemplary diverter valve arrangement exemplifying one embodiment of a potential diverter valve set 61 and 62 or 71 and 72, which in the depicted example is an electromechanical arrangement. For example, each diverter valve 61, 62, 71, 72 may be a two-position three-way valve. FIG. 9A depicts the valve set in a closed position where gas flow is maintained within the portable ventilator 2. FIG. 9B depicts the valve set in an open position where gas flow is diverted to the host 10, be it an anesthesia host 10c comprising a circle system, an ICU host 10b comprising additional ventilation control element, or any other type of host where gas flow is exchanged from the portable ventilator 2 into a ventilation path portion 100 of the host 10.

In FIG. 9A, the gas flow path (be it the inspiratory gas flow in the inspiratory path 60 or the expiratory gas flow in the expiratory path 70) passes through the inlet 130 which is open due to the diverter valve 61, 71 being in the closed position. The gas flowing through the inlet 130 travels through the passage way 60a, 70a to the outlet 132, which is open because the diverter valve 62, 72 is in the closed position, closing off the passage way to any connected host. In certain embodiments, the valves 61, 71 and 62, 72 are normally-closed-type valves which remain closed when not powered or otherwise actuated. FIGS. 9A and 9B show electromechanical valves that are electrically actuated, where each valve is associated with an actuator 134 that when electrically powered actuates, and thus opens, the normally-closed valve. In other embodiments, each set of valves 61 and 62, 71 and 72 may have an associated actuator that simultaneously actuates both valves in the set.

In electrically actuated embodiments, each valve 61, 62, 71, 72 may be a normally-closed solenoid valve that opens when power is applied to the valve. FIG. 9A shows the actuators 134 not energized, and thus the valve flaps 161, 171, 162, 172 are in a first position, the closed position which maintains the flow path within the ventilator 2 through path portion 60a, 60a in the patient interface section 6. When the actuators 134 are energized, as illustrated in FIG. 9B, the valve flaps 161, 171, 162, 172 are then moved to a second position, the open position that permits the ventilation gas to flow to a host 10. FIG. 9B depicts the electromechanical valves 61, 71 and 62, 72 in an open, or actuated, position where the gas flow flows through inlet 131 into the flow path portions 60b, 70b that lead to the host 10. In the open position, as it is referred to herein, the bypass path 60a, 70a, between the valves 61, 71 and 61, 72 is closed off such that ventilation gases do not flow between the valves 61, 71 and 61, 72 without entering the host 10. The gas flows through the pneumatic portion of the host and back up to the ventilator 2 through the outlet 133 to continue along the inspiratory path 60 or the expiratory path 70, whatever the case may be.

Figure 9C:
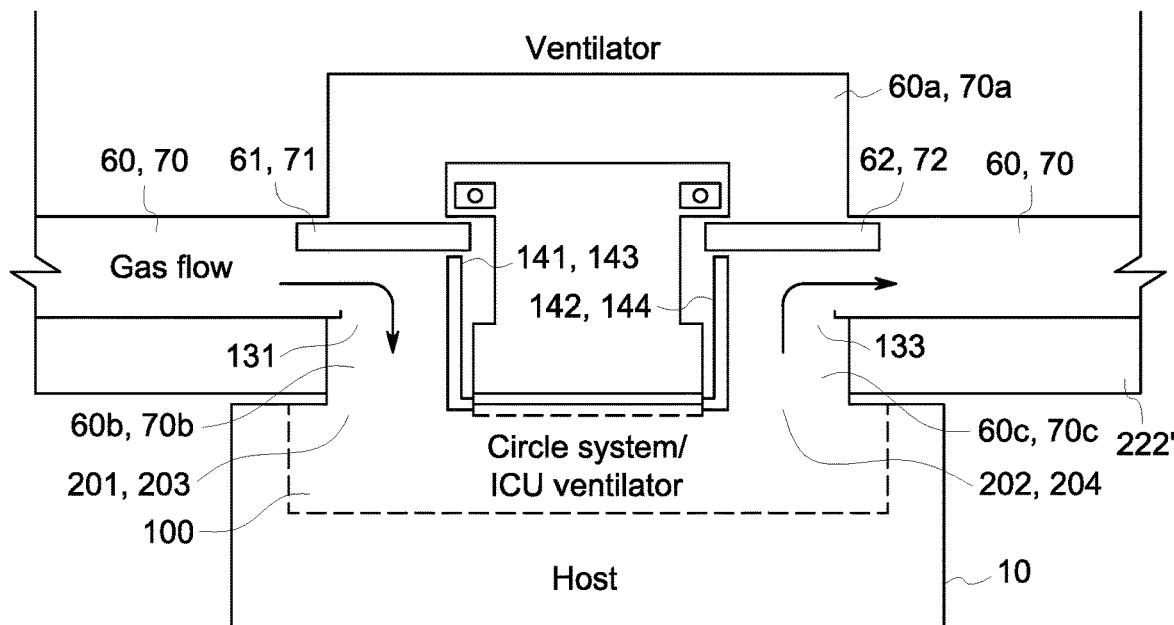
FIG. 9C depicts another embodiment of a set of diverter valves in a second position where the ventilator is connected to a host.

As described above, the valves 61, 62, 71, 72 may be mechanically actuated valves where the valves 61, 71 and 62, 72 are mechanically moved into an open position when the ventilator 2 gets connected to the host 10. FIG. 9C illustrates one embodiment where valve flaps 161, 171, 162, 172 are mechanically moved upward, such as by the above-described actuator projections 141-144 on the host housing 48. The actuator projections 141-144 are inserted into the ports 201-204 in the ventilator housing 222 when the ventilator 2 is placed on the host 10, thus forcing the valves open and permitting gas to flow into the ventilation path portion 100 of the host.

Figure 10:
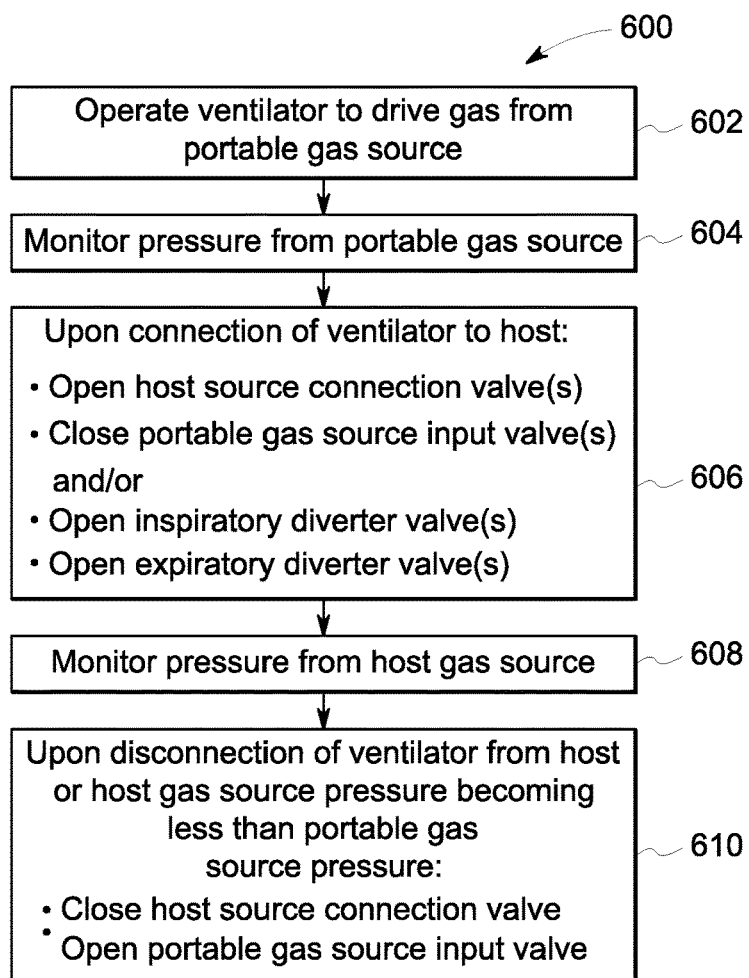
FIG. 10 is a flow chart illustrating one embodiment of a method of operating a portable ventilator according to the present disclosure.

FIG. 10 depicts one embodiment of a method 600 of ventilator operation where a portable ventilator is first operated on its own to deliver ventilation gas from a portable gas source and then, upon connection to a host, to deliver ventilation from a host gas source. A ventilator 2 is operated to drive gas from a portable gas source (e.g., 8b) to a patient at step 602. Pressure of ventilation gas from the portable gas source is monitored at step 604, such as measured by pressure sensor 33 within the vent drive 4. Upon connection of the ventilator 2, various valves open and close and step 606 in order to facilitate pneumatic connection to the host gas source 12 and/or connection to the inspiratory and expiratory pathways in the host 10, as appropriate depending on the host type. For example, connection to the host is facilitated by opening the connection valves 28 and 88b and automatically closing the gas source input valves 34a and/or 34b, as appropriate. As described above, in one embodiment the input valves 34a and/or 34b are each a check valve. For embodiments where the host includes a ventilation path portion 100, connections of the inspiratory and/or expiratory pathways to the host may also be facilitated by opening the inspiratory diverter valves (e.g. 61 and 62) and opening the expiratory diverter valves (e.g. 71 and 72).

A pressure from the host gas source is then monitored at step 608, such as measured at pressure sensor 85 in the host gas delivery section 95. Upon this connection of a ventilator from the host and/or upon the pressure of the host gas source 12 becoming less than that of the portable gas source 8, the ventilator 2 switches back to the portable gas source 8 to provide inspiratory gas to be delivered to the patient. As described above, in certain embodiments the ventilator 2 may be configured to provide inspiratory gas from the connected gas source having the greatest delivery pressure of ventilation gas and the switching occurs automatically by the check valve 34b opening and check valve 83b closing. Thus, if the host gas source becomes depleted or the ventilator 2 is disconnected from the host 10, then the pressure of the host gas source drops below that of the portable gas source causing the ventilator 2 to flip back to the portable gas source 8 for ventilating the patient. When that occurs, the host gas source connection valve 28 the ventilator 2 may remain open to support the on/off valve 94 or fresh gas 02 supply while one or more of the gas source input valves 34a or 34b opens. Additionally, if the ventilator 2 is disconnected from the host 10 and the host provides a ventilation path portion 100 that connects to the inspiratory or expiratory paths, and the respective diverter valves 61, 62, 71, 72 will close.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A ventilator system comprising:
   a ventilator comprising:
      a ventilation drive configured to drive ventilation gas from a gas source to a patient and a patient interface section configured to form an inspiratory path for inspiratory gas from the ventilation drive to a patient connection, and an expiratory path for expiratory gas from the patient connection out of the ventilator;
      wherein the patient interface section comprises an interface housing having an inspiratory connection port and an expiratory connection port configured to connect to tubing of the patient connection, wherein the patient connection comprises the tubing connected to a patient end connector;
      wherein the interface housing of the patient interface section is configured to releasably connect to a ventilation drive housing of the ventilation drive;
   a host comprising a host gas source; and
   wherein the ventilator is configured to removably connect to the host such that the interface housing and the ventilation drive housing connect to the host;
   wherein the ventilator is configured such that when the ventilator is removably connected to the host, the ventilation drive drives the inspiratory gas from the host gas source through the patient interface section to the tubing of the patient connection and at least one of the inspiratory path and the expiratory path connect to the host such that at least one of the inspiratory gas and the expiratory gas are diverted through the host, and when the ventilator is not connected to the host, the ventilation drive drives the inspiratory gas from a portable gas source through the patient interface section to the tubing of the patient connection.

2. The system of claim 1, wherein the patient interface section releasably connects to the host such that the inspiratory path and the expiratory path are diverted to the host.

3. The system of claim 2, wherein the host is an anesthesia host comprising a circle breathing system that connects to both the inspiratory path and the expiratory path, wherein the circle breathing system is configured to introduce anesthetic gas from an anesthetic gas source to the inspiratory path.

4. The system of claim 3, wherein the patient interface section and the circle breathing system are configured to releasably connect together.

5. The system of claim 4, wherein the patient interface section and the circle breathing system are configured to be removed from the ventilation drive and the anesthesia host as a connected unit.

6. The system of claim 5, wherein the ventilation drive comprises a ventilation drive housing
wherein the circle breathing system comprises a circle section housing;
wherein the circle section housing and the interface housing are configured to releasably connect together.

7. The system of claim 6, wherein interface housing and the circle section housing are each cleanable and sterilizable units.

8. The system of claim 1, wherein the expiratory path does not enter the ventilation drive such that the ventilation drive does not receive any patient expiratory gas.

9. The system of claim 8, wherein the patient interface section is separately removable from the ventilator system while the ventilation drive is connected to the host and is a cleanable and sterilizable unit.

10. The system of claim 1, wherein the patient end connector is one of an endotracheal tube, a mask, or a nasal cannula.

11. The system of claim 1, wherein the interface housing of the patient interface section is configured to releasably connect to the host such that the inspiratory path and the expiratory path are diverted to the host.

12. A ventilator comprising:
a ventilation drive configured to drive ventilation gas from a gas source to a patient;
a patient interface section configured to form an inspiratory path for inspiratory gas from the ventilation drive to a patient connection, and an expiratory path for expiratory gas from the patient connection out of the ventilator;
wherein the patient interface section comprises an interface housing having an inspiratory connection port and an expiratory connection port configured to connect to tubing of the patient connection, wherein the patient connection comprises the tubing connected to a patient end connector;
wherein the interface housing of the patient interface section is configured to releasably connect to a ventilation drive housing of the ventilation drive; and
wherein the ventilation drive is configured to removably connect to a host such that when the ventilation drive is connected to the host the ventilation drive is configured to drive the inspiratory gas from a host gas source through the patient interface section to the patient, and when the ventilation drive is not connected to the host the ventilation drive is configured to drive the inspiratory gas from a portable gas source through the patient interface section to the patient.

13. The ventilator of claim 12, wherein the patient interface section also releasably connects to the host such that at least one of the inspiratory path and the expiratory path are diverted to the host.

14. The ventilator of claim 13, wherein the host is an anesthesia host comprising a circle breathing system that connects to both the inspiratory path and the expiratory path, wherein the circle breathing system is configured to deliver anesthetic gas to the inspiratory path.

15. The ventilator of claim 14, wherein the circle breathing system comprises a circle section housing that releasably attaches to a host gas delivery section of the host;
wherein the patient interface section comprises an interface housing, wherein the circle section housing and the interface housing are configured to releasably connect together.

16. The ventilator of claim 15, wherein the interface housing and the circle section housing are configured to be removed from the ventilation drive and the host as a connected unit.

17. The ventilator of claim 15, wherein the ventilation drive comprises a ventilation drive housing the ventilation drive housing including at least a drive housing connector; and
wherein the interface housing includes at least an interface housing connector configured to releasably mate with the drive housing connector so as to releasably connect the patient interface section to the ventilation drive and a vent housing connector configured to releasably mate with a host housing connector on the circle section housing.

18. The ventilator of claim 12, wherein the expiratory path does not enter the ventilation drive such that the ventilation drive does not receive any patient expiratory gas.

19. The ventilator of claim 12, wherein the ventilation drive comprises a blower within the ventilation drive housing that drives the inspiratory gas along an inspiratory drive path.

20. The ventilator of claim 12, wherein the ventilation drive housing includes at least a drive housing connector; and
the interface housing includes at least an interface housing connector configured to releasably mate with the drive housing connector so as to releasably connect to the ventilation drive.

21. The ventilator of claim 12, wherein the ventilation drive housing further includes a first inspiratory connection port; and
wherein the interface housing further includes a second inspiratory connection port configured to mate with the first inspiratory connection port to connect an inspiratory drive path in the ventilation drive to the inspiratory path in the patient interface section.

* * * * *